United States Patent
Corning

(10) Patent No.: US 9,938,026 B1
(45) Date of Patent: Apr. 10, 2018

(54) ENERGY BEAM PROPULSION SYSTEM

(71) Applicant: Michelle Corning, Flagstaff, AZ (US)

(72) Inventor: Michelle Corning, Flagstaff, AZ (US)

( * ) Notice: Subject to any disclaimer, the term of this patent is extended or adjusted under 35 U.S.C. 154(b) by 0 days.

(21) Appl. No.: 15/651,398

(22) Filed: Jul. 17, 2017

Related U.S. Application Data

(63) Continuation-in-part of application No. 15/167,737, filed on May 27, 2016, now Pat. No. 9,711,252, which is a continuation-in-part of application No. 14/925,970, filed on Oct. 28, 2015, now Pat. No. 9,508,460, which is a continuation-in-part of application No. 14/525,506, filed on Oct. 28, 2014, now Pat. No. 9,269,470.

(51) Int. Cl.
| | |
|---|---|
| *F03H 99/00* | (2009.01) |
| *B64G 1/40* | (2006.01) |
| *F02K 99/00* | (2009.01) |
| *H05H 3/06* | (2006.01) |
| *G21K 1/093* | (2006.01) |
| *G21K 1/06* | (2006.01) |

(52) U.S. Cl.
CPC ............. *B64G 1/409* (2013.01); *F03H 99/00* (2013.01); *G21K 1/06* (2013.01); *G21K 1/093* (2013.01); *H05H 3/06* (2013.01)

(58) Field of Classification Search
USPC ........... 250/251, 269.6, 492.1, 526; 376/105, 376/106, 107, 114, 158, 463; 60/172, 60/250, 251, 259
See application file for complete search history.

(56) References Cited

U.S. PATENT DOCUMENTS

| | | | |
|---|---|---|---|
| 3,752,989 A | 8/1973 | Motz et al. | |
| 4,172,979 A | 10/1979 | Morrison | |
| 4,516,535 A | 4/1985 | Russell, Jr. et al. | |
| 4,891,600 A * | 1/1990 | Cox | F03H 99/00 250/251 |
| 5,658,233 A | 8/1997 | Peurrung | |
| 6,968,676 B1 * | 11/2005 | Krishnan | C06B 45/00 60/250 |
| 7,194,063 B2 | 3/2007 | Dilmanian et al. | |
| 7,194,852 B1 * | 3/2007 | Krishnan | F02K 7/10 60/250 |
| 7,310,408 B2 | 12/2007 | Filkins et al. | |
| 7,312,461 B2 | 12/2007 | Lewellen et al. | |
| 7,345,291 B2 | 3/2008 | Kats | |
| 7,506,500 B1 * | 3/2009 | Krishnan | F02K 9/10 60/250 |

(Continued)

*Primary Examiner* — Bernard Souw
(74) *Attorney, Agent, or Firm* — Invention To Patent Services; Alex Hobson

(57) ABSTRACT

A spacecraft is propelled by a high energy beam propulsion device that emits a high energy beam, such as a neutron beam, from the spacecraft. The high energy beam propulsion device has a neutron beam source and a neutron beam generator that emits the neutron beam through a magnetic coil. The magnetic coil may be a discrete coil or extend over a length of the neutron beam length. The magnetic coil may be self-contained and utilize natural magnets or may be a powered magnet, wherein the magnetic field is produced by a flow of electrical current. The neutron source may be powered or self-contained and utilizes neutron emitting materials including Californium-252, Cesium-137, and Polonium-Beryllium.

20 Claims, 30 Drawing Sheets

(56) References Cited

U.S. PATENT DOCUMENTS

| | | | |
|---|---|---|---|
| 7,463,610 B2 | 1/2010 | Dilmanian | |
| 8,031,824 B2 * | 10/2011 | Bystriskii | G21B 1/052 |
| | | | 376/107 |
| 8,173,983 B1 | 5/2012 | Sahadevan | |
| 8,915,833 B1 | 12/2014 | Sahadevan | |
| 9,008,271 B2 | 4/2015 | Burshtein et al. | |
| 9,126,036 B2 | 9/2015 | Leek | |
| 9,180,985 B1 * | 11/2015 | Hardy | B64G 1/408 |
| 9,269,470 B1 * | 2/2016 | Corning | H05H 3/06 |
| 9,346,565 B1 * | 5/2016 | Hardy | B64G 1/408 |
| 9,508,460 B1 * | 11/2016 | Corning | A61N 5/1084 |
| 9,711,252 B1 * | 7/2017 | Corning | G21K 1/06 |
| 2003/0226401 A1 * | 12/2003 | Letovsky | G01N 37/005 |
| | | | 73/579 |
| 2005/0145031 A1 * | 7/2005 | Letovsky | G01N 37/005 |
| | | | 73/579 |
| 2008/0153131 A1 | 6/2008 | Jakobsen et al. | |
| 2009/0088625 A1 | 4/2009 | Oosting et al. | |
| 2009/0108192 A1 * | 4/2009 | Groves | H05H 3/06 |
| | | | 250/269.4 |
| 2011/0006224 A1 | 1/2011 | Maltz et al. | |
| 2013/0066135 A1 | 3/2013 | Rosa et al. | |
| 2013/0148770 A1 | 6/2013 | Mofakhami et al. | |
| 2014/0249348 A1 | 9/2014 | Mazin | |
| 2014/0328461 A1 | 11/2014 | Gertner et al. | |
| 2015/0098544 A1 * | 4/2015 | Blanovsky | G21C 1/28 |
| | | | 376/246 |

* cited by examiner

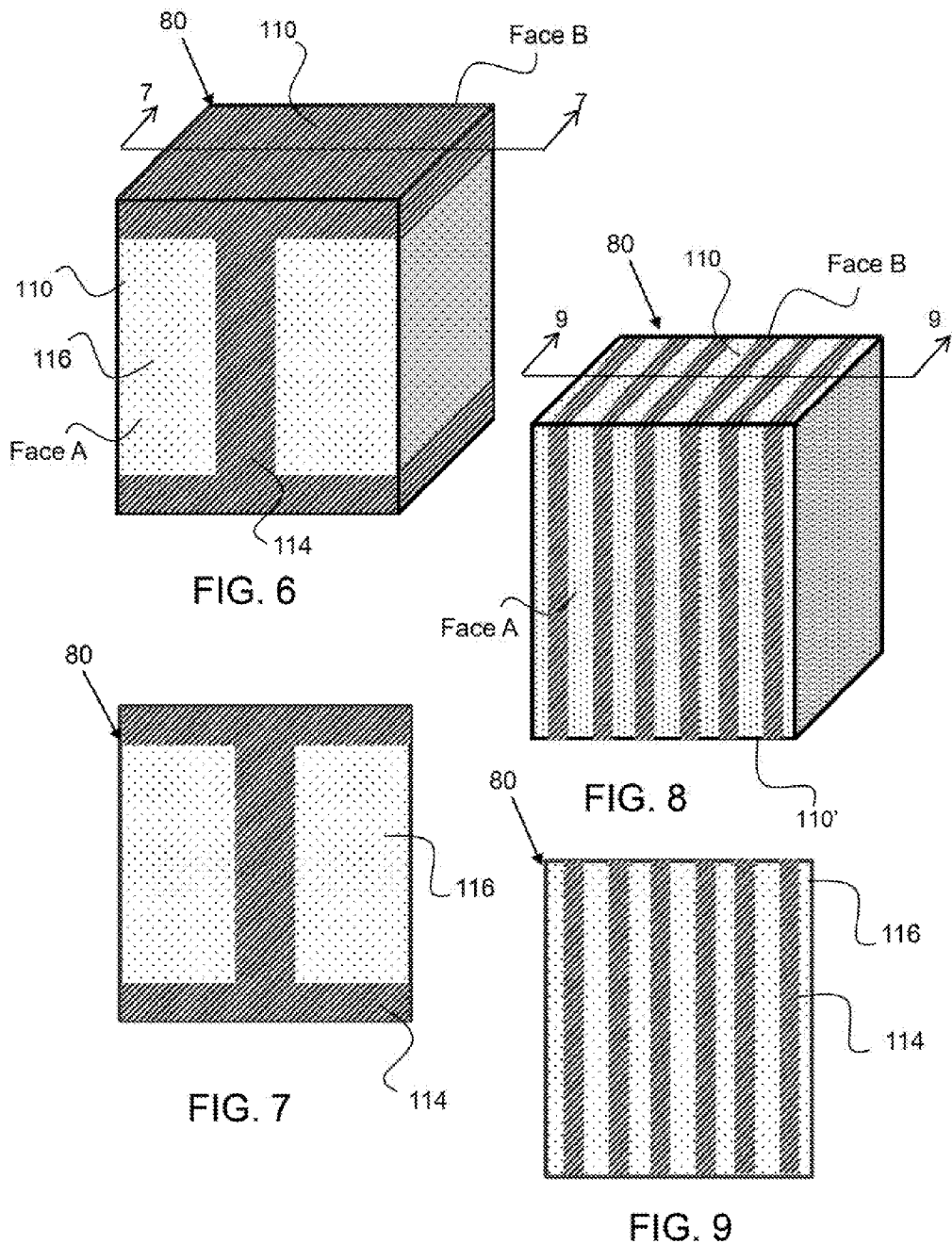

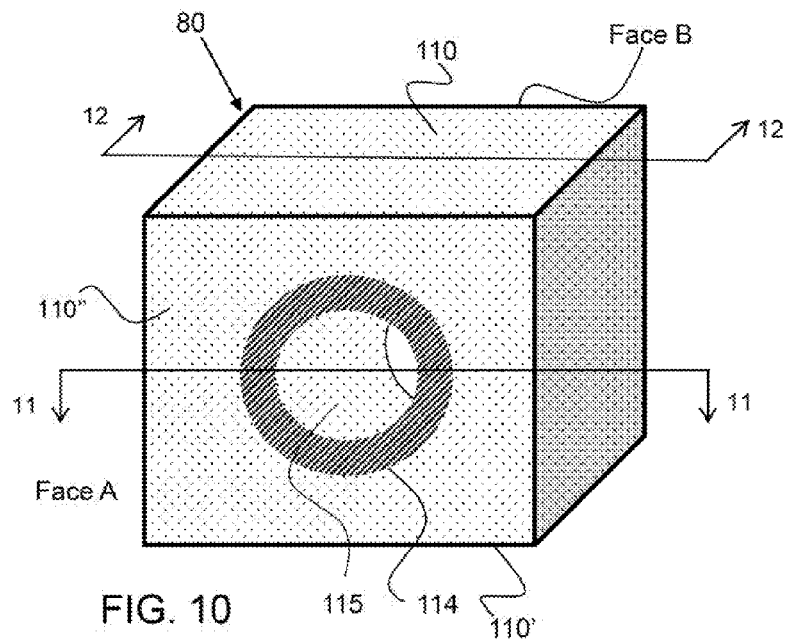
FIG. 10
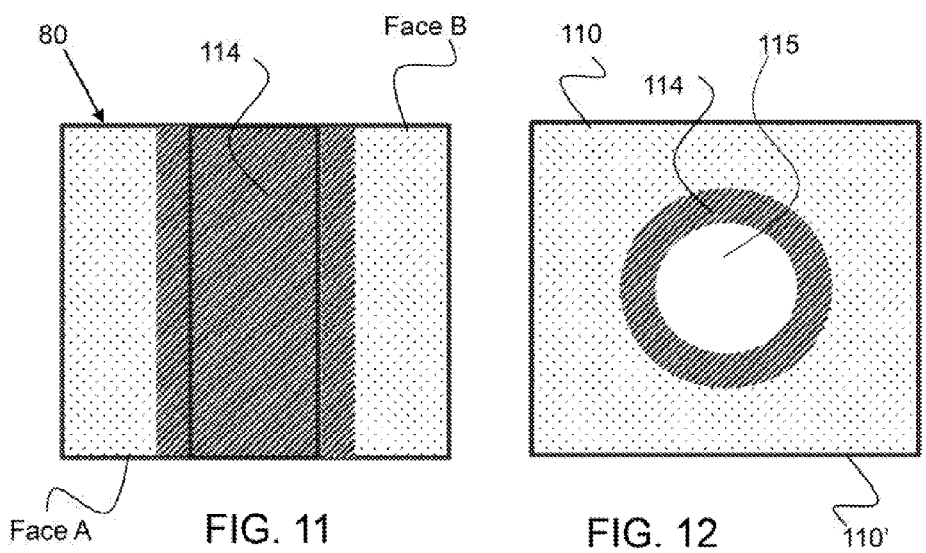
FIG. 11
FIG. 12

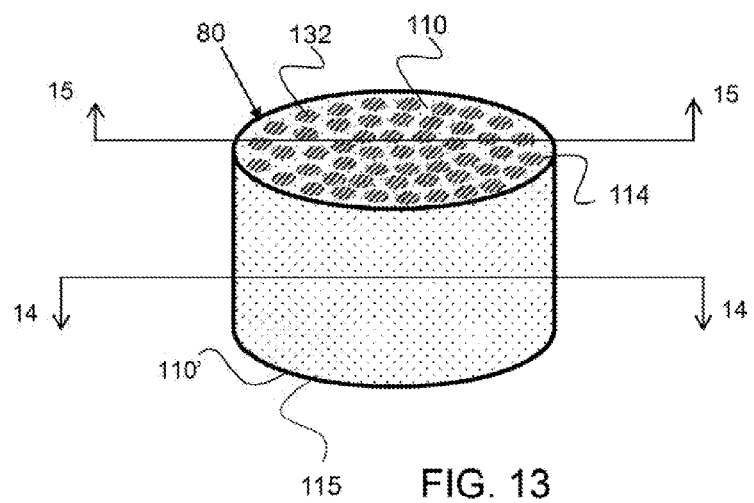
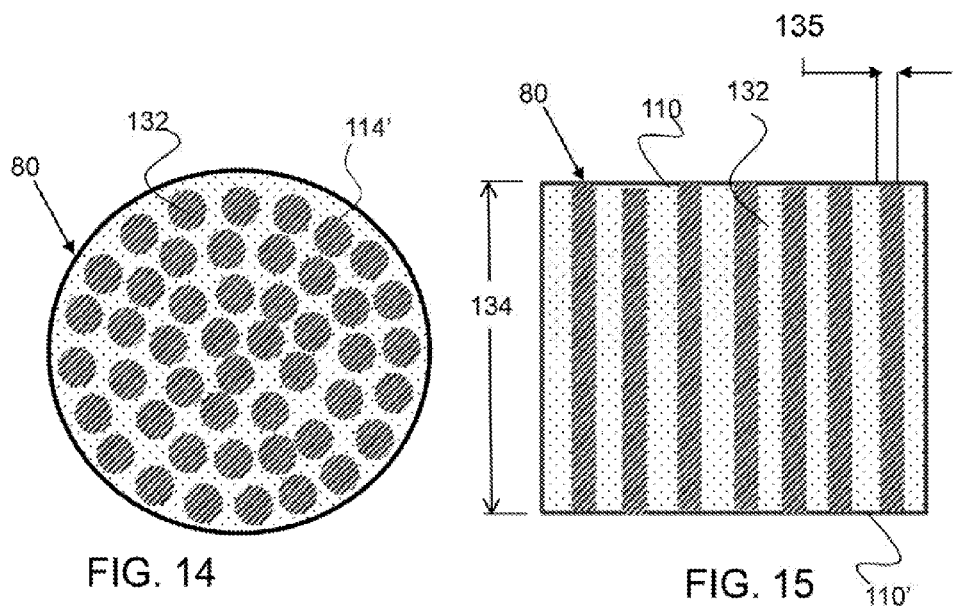

ENERGY BEAM PROPULSION SYSTEM

CROSS REFERENCE TO RELATED APPLICATIONS

This application is a continuation in part of U.S. patent application Ser. No. 15/167,737 filed on May 27, 2016 and entitled High Energy Beam Diffraction Material Treatment System and currently pending, which claims the benefit of U.S. patent application Ser. No. 14/925,970, filed on Oct. 28, 2015, entitled Neutron Beam Diffraction Material Treatment System and now issued as U.S. Pat. No. 9,508,460 on Nov. 29, 2016, which is a continuation in part of U.S. patent application Ser. No. 14/525,506, filed on Oct. 28, 2014, entitled Neutron Beam Regulator and Containment System, and now issued as U.S. Pat. No. 9,269,470 on Feb. 23, 2016; the entirety of all applications listed above are incorporated by reference herein.

BACKGROUND OF THE INVENTION

Field of the Invention

The present invention relates to coherent beam treatment system that produces a first and second energy beam that are coherent at a treatment location.

Background

High energy beams are used for a wide variety of treatment applications including material treatment, such as the treatment of plastics and metals, and organic tissue treatment, such as the treatment of tumors. High energy beams include acoustic beams or waves, neutron beams, proton beams, lasers, and x-rays, that may be defined by a wave. In many treatment applications, a beam is passed through a person's body to a treatment location. The beam passes through the body and is incident on the treatment location, such as a tumor. All of the tissue that the beam passes through is being exposed to the high energy beam and this may not be desirable. In other applications, a first and second beam may be configured to intersect at a treatment location, as described in U.S. patent application Ser. No. 14/525,506, filed on Oct. 28, 2014, entitled Neutron Beam Regulator and Containment System. The beams may diffract and the diffraction may increase the effectiveness of the treatment.

High energy beam may be used in a variety of applications including analytical methods, cancer treatment and to treat or condition various materials. For example, neutron beams are used for scattering and diffraction material analysis of material properties and particularly the crystallinity of a material. The highly penetrating nature of neutron beams may be used in the treatment of cancerous tumors. Another use of neutron beams may be to treat materials, and particularly metals, wherein neutron bombardment lodges neutrons into the metal to effectively harden the metal. Neutron bombardment can create point defects and dislocations that stiffen or harden the materials. These and other uses of neutron beams can potentially expose people to neutron radiation and neutron activation, the ability of neutron radiation to induce detrimental high energy in body tissue or other substances and objects exposed thereto.

Neutron beam radiation protection generally utilizes radiation shielding, or placing a material around the beam, beam source and target that absorbs neutrons. Common neutron shielding materials include high molecular weight hydrocarbons such as polyethylene and paraffin wax, as well as concrete, boron containing materials including boron carbide, boron impregnated silica glass, borosilicate glass, high-boron steel, and water and heavy water. These shielding materials have varying levels of effectiveness and can become radioactive over time, thereby requiring them to be changed out. In addition, a shield may not be installed or properly positioned during use of a neutron beam, thereby exposing workers and the surrounding environment to neutron radiation.

Neutrons can be guided by a vacuum tube having an inner surface coated with a neutron reflector, such as nickel. This reduces the loss of neutrons through scattering of the beam. Although neutron guides can transport neutron beams, they do not act to focus or reduce beam divergence. Magnetic fields can be used to affect a neutron beam shape, intensity, velocity, direction and polarization. Magnetic fields generated by an electrical current running through a coil, for example, may be used to direct, intensify and contain a neutron beam. However, a neutron beam source, such as a neutron beam generator, may be operated independently of an electrical current generated magnetic field configured to direct and otherwise contain a neutron beam, leaving the system susceptible to operating in an unsafe condition when no other containment system is employed.

Materials or parts hardened through neutron bombardment may only require hardening over a particular area, or a higher degree of hardening in a particular region of the part. Current neutron bombardment systems provide a uniform dosing of neutrons to the material or part and do not enable a gradient of hardening.

SUMMARY OF THE INVENTION

The present invention describes a coherent beam treatment system that produces a first and second energy beam that are coherent at a treatment location. An energy beam, as used herein, includes a neutron beam, a proton beam, an electron beam, acoustic waves, a laser and x-ray. A high energy beam, or simply beam used herein, may be defined by a wave, such as a sinusoidal wave having a frequency and amplitude. The present invention provides a control system for creating coherence between a first and second beam at a treatment location. Coherence is a location where two waves have matching wave profiles. As an example, coherence between two waves wherein a first wave has a frequency that is double that of the second wave occurs at every other peak of the first wave. A wave may be defined by a simple sinusoidal equation wherein the frequency and amplitude are constant as a function of time. The present invention may regulate one of both beams to be defined by a complex wave equation, wherein the frequency and/or amplitude change as a function of time. A complex wave may be the culmination of two or more wave equations, as defined by Fourier Transform, for example. A control system of the present invention may regulate one or both beams to be coherent at a treatment location and may modify the location of coherence to allow treatment over a treatment area.

The Fourier transform is called the frequency domain representation of an original signal or wave. The term Fourier transform refers to both the frequency domain representation and the mathematical operation that associates the frequency domain representation to a function of time. A Fourier transform may define a wave form that changes amplitude and/or frequency as a function of time and this is referred to herein as a complex wave form, and the equation defining the wave form is defined as a complex wave form equation. A complex wave equation may be combination of two or more wave equations. The control system may employ a computer program that utilizes complex wave equations, Fourier transforms and the like to produce a high energy beam that is a complex wave, as defined herein.

In an exemplary embodiment, a coherent beam treatment system produces a first energy beam having a first frequency and a first direction and a second energy beam having a second frequency and a second direction. The control system comprises a beam regulator configured to adjust the frequency of the first beam and/or second beam to create first and second beam coherence at a treatment location. The control system may comprise an actuator that changes the direction of the first and/or second beam being emitted, and therefore may change the location of coherence. In this way, an area over a treatment location may be treated by movement of one or more of the beam. An actuator may rotate a beam and a direction of a second beam may be kept constant, thereby changing the location of intersection of the two beams along the length of the second beam. In addition, the control system may regulate first or second beam, such that the location of coherence corresponds substantially with the location of intersection of the two beams.

A beam regulator may receive input from a microprocessor that regulates a beam's frequency and/or amplitude as a function of time. A beam may be defined by a complex wave, wherein the amplitude and/or frequency change as function of time. The wave equation may be the culmination of two or more simple wave equations, each with their own frequency and amplitude. Fourier Transform may be utilized by a control system program to provide instruction to the regulator to control the wave produced.

A first high energy beam may be substantially different from a second energy beam, wherein a first energy beam has a frequency and/or amplitude that is at least 20% different than the second energy beam. A first high energy beam may an amplitude and or frequency that is different from a second high energy beam by about 20% or more, about 30% or more, about 50% or more, about 100% or more, about 200% or more, about 500% or more and any range between and including the difference percentage provided. In an exemplary embodiment, the first energy beam has an amplitude and/or frequency that is at least twice that of the second energy beam. The first and second beams may be substantially different at a treatment location or at a location of coherence. In one embodiment, the first and second beams are defined by a simple wave equation, having a constant frequency and amplitude as a function of time. In another embodiment, one of the first or second energy beams are defined by a simple wave equation and the other is defined by a complex wave equation, again, having a change in amplitude or frequency as a function of time. In still another embodiment, both the first and second energy beams are defined by a complex wave equation.

In an exemplary embodiment, a coherent beam treatment system comprises a first and a second beam generator, wherein at least one has a beam regulator. In another embodiment, both the first and second beams generators are configured with a beam regulator to change the frequency and/or amplitude of the beams. In still another embodiment, a beam generator produces an input beam that is then split by a beam splitter into a first split beam and second split beam. The first and/or second split beams may travel from the beam splitter to a reflector, that directs the first and second beams to intersect or substantially align at a treatment location. Substantially align, as used herein, means that the first and second beams are close enough to have coherence. A beam splitter may incorporate one or more prisms and a reflector may comprise a mirror. In an exemplary embodiment, a second split beam is reflected by a mirror and is directed toward a treatment location. A split beam may be further regulated by a beam regulator. For example, a split beam may be regulated by a beam regulator that is configured after the reflector, or mirror.

An exemplary coherent beam treatment system comprises a user interface. The user interface may allow a user to set or input a treatment location, may enable an input of power output of the energy beams, may enable input of treatment time or protocol. A treatment location may be identified on a mapped area, such as an x-ray of a person body. For example, treatment location may be identified on an X-ray or other image produced by an imaging technique. The control system may then automatically control the beams to be coherent at the treatment location, or in an area around the treatment location. A user may outline a treatment location and the control system may generate coherence of the two beams over the outlined treatment location. Furthermore, beams may be affected by a material that the beam has to pass through and the user interface may enable an input of a material type and the control system may automatically adjust the beams to effectively pass through the material and be coherent at a treatment location.

A high energy beam may be a proton beam, neutron beam, laser or X-rays. The type of high energy beam used may be selected for the best effectiveness of the treatment desired.

The present invention provides for a method of treating a treatment location by creating high energy beam coherence at said treatment location, as described herein. The treatment location may be a surface of a material, such as a metal or plastic. In another embodiment, the treatment location is organic material, such as a part of a body, human or animal. In an exemplary embodiment, a treatment location is a tumor and the treatment destroys the tumor or sufficiently damages the tumor tissue to destroy the viability of cells therein. For cancer tumor treatment, the high energy beams described herein provide a treatment option that does not require radiation, or a radioactive source. This eliminates the risk of loss of a radioactive material that may be used in terrorist activity.

The invention is directed to a neutron beam diffraction treatment system and method of treating a work-piece. In an exemplary embodiment, a neutron beam diffraction material treatment system comprises a first neutron beam source configured to produce a first neutron beam having a first direction and a second neutron beam source configured to produce a second neutron beam having a second direction, wherein the second neutron beam Intersects with the first neutron beam at an intersecting point and whereby the first and second beams are diffracted as a result of intersecting each other. In an exemplary embodiment, the intersecting point of the diffracted beams is located on a within a work-piece to treat the work-piece. The work-piece may be treated by neutron entrapment or through localized heating. The intersecting point may be configured to move on or within the work-piece such as by movement of the work-piece by an actuator, or by controlled movement of the first and second neutron beams, or coordinated actuation.

The intensity of the first and or second neutron beams may be change or varied in a modulating manner to produce a changing treatment intensity. One or more magnetic coils may extend around the neutron beam from the neutron beam source, or outlet of the source, to the work-piece or target. The intensity of the magnetic field may be changed or modulated to affect the neutron beam and thereby modulate the neutron beam or the diffraction properties. A magnetic coil may also be used to ensure containment of the neutron beam, as described further herein.

A work-piece may be plastic and work-piece treatment may include localized heating of the plastic surface or a portion within work-piece, such as below the surface. A work-piece may be metal, or metal alloy and treatment of the work-piece may include neutron entrapment.

An exemplary neutron beam diffraction material treatment system may comprise a magnetic coil configured to extend around one or each of the neutron beam and may be configured to extend around both of the neutron beams. A magnetic coil may extend from the neutron beam source to the work-piece or work-piece station and thereby contain the neutron beam. The magnetic coil may be a continuous magnetic coil or a discrete magnetic coil. In one embodiment, a magnetic coil extends around both of the neutron beams. The magnetic field produced by the magnetic coil may be configured with a power control system to ensure that the neutron beam will not operate unless the magnetic field is activated and operational, thereby ensuring containment of the neutron bean. In an exemplary embodiment, the magnetic field strength on the neutron bean is changed or modulated as a function of time. This may be accomplished by changing the strength of the magnetic field produce, such as by the amount of current drawn by the magnetic coil or by changing a position of the magnetic coil with respect to the neutron beam. The magnetic coil may be moved or oscillated to vary the magnetic field on the neutron beam, for example.

Neutrons have a magnetic moment and can be affected by exposure to magnetics fields. The shape, intensity, velocity, direction and polarization of a neutron beam can be manipulated through magnetic field exposure. In an exemplary embodiment, a neutron beam regulator, or the present invention, comprises a magnetic coil configured around a neutron beam between a neutron beam source and a target. A magnetic coil may extend substantially the entire distance between a neutron beam source, or outlet of the beam source, and a target. In an exemplary embodiment, a magnetic coil is configured to extend at least partially around a neutron beam source to further contain and direct the neutrons and thereby reduce neutron radiation exposure outside proximal to the beam source. In another exemplary embodiment, a magnetic coil is configured to extend at least partially around a target. For example, a target may be configured to fit within a work piece station and a magnetic coil may extend around a portion of the work-piece station. A work-piece station may be configured to index in and out of a magnetic coil, whereby a work-piece can be loaded into the work-piece station and then positioned at least partially with the magnetic coil or magnetic field produced by the coil. Again, configuring the magnetic coil and/or directing the field around a work-piece will further contain and direct the neutrons and thereby reduce neutron radiation proximal to the target or outside of a target area.

In an exemplary embodiment, a neutron beam regulator comprises a power control system that is configured as a safety system to ensure that the neutron beam is not operational unless a containing magnetic coil is powered on. An exemplary power control system comprises a magnetic coil power supply output, a neutron beam source power supply output, a magnetic coil power sensor, and a power safety feature. The power safety feature ensures that the neutron beam generator will not receive power from the power control system unless the magnetic coil is receiving power and producing a confining magnetic field, thereby effectively containing the neutron beam. A magnetic coil power supply sensor is configured to detect when the magnetic coil is operating and the power safety feature is configured to prevent power supply to said neutron beam source power supply output unless the magnetic coil power supply sensor detects that the magnetic coil is on. In embodiments with a plurality of discrete magnetic coils that may have their own coil power output, a single power supply may be configured to power each of the coil power outputs. A magnetic coil power sensor may be configured with this single power supply. The power supply to a neutron beam source power supply output may be cut-off by any suitable means including a switch that is opened in the event that the magnetic coil sensor detects that no power is being delivered to the magnetic coil(s).

Any suitable type of magnetic coil may be configured around a neutron beam including a continuous magnetic coil and discrete magnetic coils. A magnetic field may be generated by electromagnets, or any suitable electrical current carrying material. In an exemplary embodiment, a magnetic coil comprises an electrically conductive wire that extends completely around the neutron beam, or 360 degrees around the beam. In some cases, a magnetic coil is configured as a discrete magnetic coil or ring that extends around the neutron beam. A discrete magnetic coil extends a portion of the neutron beam length, or distance from the neutron beam source or outlet to a target, including, but not limited to, no more than about one quarter of the neutron beam length, no more than about one third of the neutron beam length, no more than one half of the neutron beam length and any range between and including the discrete magnetic coil extension lengths. Any suitable number of discrete coils may be configured around the neutron beam including, but not limited to, 2 or more, 4 or more, 6 or more, 10 or more, twenty or more and any range between and including the number of coils provided. In another embodiment a magnetic coil is configured as a continuous coil that winds around the neutron beam in a substantially continuous manner or substantially the entire neutron beam length. A continuous coil, as defined herein, extends at least about three quarters of the neutron beam length.

A magnetic coil may comprise a single continuous wire or a plurality of wires that may be bundled or otherwise configured in a coil or ring around the neutron beam. In an exemplary embodiment, a single continuous coil is configured around a neutron beam and extends from a neutron beam source to a target. In another embodiment, a plurality of discrete coils are configured along the neutron beam between the beam source and the target.

The magnetic coils may be configured in any suitable manner around the neutron beam. In one embodiment, one or more discrete magnetic coils are configured proximal to the neutron beam and a continuous magnetic coil is configured around or outside of the one or more discrete magnetic coils. In this embodiment, the outer continuous magnetic coil may be configured primarily as a neutron beam containment coil to reduce neutron radiation leakage. In addition, in this embodiment, the one or more discrete magnetic coils may be independently powered by a beam modulator controller to provide a modulating magnetic field that is configured to change the properties of the neutron beam as desired. A beam modulator controller is configured to enable modulation of the electrical current to the discrete coils and therefore modulation of the magnetic field intensity or direction. For example, the magnetic field intensity of a first magnetic coil configured proximal to a neutron beam source may be higher, such as two times or more, the magnetic field intensity of a second magnetic coil configured more proximal to a target. The magnetic field may be modulated to change the shape, intensity, velocity, direction and polarization of a neutron beam. The magnetic field may be modulated to ensure a sufficient level of containment of the neutron beam depending on the neutron beam source or type, the length of the beam from the source to the target and the like. In addition, a magnetic field may be modulated to increase the amount of exposure of a particular incident surface. An incident surface may be a material for analysis, a material for hardening through the bombardment with a neutron beam, a patient tissue or cancer tumor location and the like. An incident surface may be plastic or metal or organic tissue.

A neutron beam regulator may comprise a work-piece station that is configured to retain a work-piece for exposure to a neutron beam configured within a magnetic field. In an exemplary embodiment, a work-piece station is configured to move and thereby move the location of the incident neutron beam on the work-piece surface. A neutron beam regulator may be configured with a modulating magnetic coil that is configured to receive a variable power input from the beam modulator controller. The work-piece may be positioned and indexed to change the location of the incident neutron beam and the intensity of the neutron beam may be modulated to enable variable conditioning or treatment of the work-piece surface. For example, a first portion of a work-piece surface may be exposed to a higher intensity beam and therefore have a higher hardness, and a second portion of a work-piece may be exposed to a lower intensity neutron beam and have a resulting lower hardness. This combination of neutron beam intensity modulation along with work-piece positioning enables complete tailoring of work-piece treatment conditions heretofore not available. This same principle may be used to also provide specific and more precise treatment of cancerous tumors, whereby the tumor itself may be exposed to a much higher neutron beam intensity than surrounding tissue. This controlled method may reduce damage to surrounding tissue and more effectively treat a tumor. The coherence of two high energy beams may be moved by a change in the Fourier transform equations used to control one or more of the beams, or may physical movement of one or more of the beams, either by displacement or by rotation. In this way, a tumor, for example, may be subjected to coherence of the two beams over substantially the entire tumor. Higher energy may be imparted into the core of central region of the tumor than around the periphery, to reduce damage to surrounding tissue.

In an exemplary embodiment, a neutron beam regulator system is configured with at least one magnetic coil that extends around a neutron beam between a neutron beam source and a target, a work-piece station and a treatment control system. A treatment control system is configured with a beam modulator controller to control the power supply to the magnetic field and therefore the intensity of the neutron beam. In addition, a treatment control system may comprise a beam location program configured to track the location of a neutron beam with respect to an incident surface, such as on a work-piece or proximal a tumor. A beam modulator controller may be configured to vary a property of a neutron beam as a function of said neutron beam location. As described, this type of system enables a tailored treatment function and this may be programmed into the treatment control system. A neutron beam regulator system comprising a treatment control system may also comprise a power control system and the treatment control system may be configured with the power control system. A one-piece unit may house both the treatment control system and the power control system.

A novel method of regulating a neutron beam source is provided by any of the embodiments of the neutron beam regulator as described herein. In one exemplary method, a neutron beam source and magnetic coil are both plugged into a power control system. The power control system is powered on thereby enabling power supply to both the magnetic coil and the neutron beam generator and thereby substantially containing the neutron beam within the magnetic coil. The magnetic coil power sensor is configured to monitor the power supply to the magnetic coil and, in the event of a loss of power being drawn by the magnetic coil, the power supply to the neutron beam source will be terminated. It is to be understood that a threshold power draw level may be set for the magnetic coil power supply output and the magnetic coil power sensor may be configured to detect a power draw below this threshold level and thereby terminate power to the neutron beam source.

The neutron beam regulator system, as described herein, may effectively keep neutrons outside of the containment and/or modulating magnetic coils, thereby creating an exclusion zone. In some environments, labs and processing facilities for example, it may be important to exclude any neutrons from entering into the exclusion zone as they may interfere with the neutron beam.

A neutron beam system, as described in any of the embodiments herein, may be configured on a spacecraft as a neutron beam propulsion device, wherein the emission of a neutron beam from the spacecraft propels the spacecraft. The neutron beam propulsion device may comprise one or more magnetic coils around the emitted neutron beam and the magnetic coils may be discrete or may be continuous, wherein they extend from the neutron beam generator along at least a portion of the length of the beam that is 10 cm or more. The magnetic may be powered magnets or self-contained magnets. Powered magnets require electrical power to produce the magnetic field, wherein an electric current flows through the coils to produce a magnetic field of varying intensity depending on the current flow. A self-contained magnet may be a natural magnet that produces a magnetic field without the supply or electrical power and may comprises neobdium, for example. The neutron power source may be self-contained or generated, wherein electrical power is required for generate the neutron beam. A self-contained neutron beam source produces neutrons naturally such including, but not limited to, a radioactive material, Californium-252, Cesium-137 and polonium-beryllium (Po—Be). The neutrons produce naturally may form a neutron beam through the neutron beam generator. A spacecraft utilizing a self-contained neutron beam source and a self-contained magnetic coil may be a self-contained spacecraft, or a space-craft requiring no external or consumable fuel supply. A self-contained spacecraft may be capable of travel through large distances of space for data gathering missions, for example.

Cesium-137, or radiocaesium, is a radioactive isotope of cesium. Cesium is a fission product of nuclear fission of uranium-235 or other isotopes in nuclear reactors. Cesium-137 emits neutron and has a half-life of about 30 years.

Polonium is an alpha emitter having a half-life of 138.4 days and decays to the stable isotope. Pb. Polonium has an alpha form having a simple cubic crystal structure in a single atom basis and a beta form that is rhombohedral. Polonium, such as polonium-210 in the presence of beryllium emits neutrons. A mixture of polonium with beryllium (Po—Be) emits neutrons. Alternatively.

Californium is radioactive chemical element with symbol Cf and atomic number 98. Isotopes of californium emit neutrons and californium is used to aid in the start-up of nuclear reactors, and for neutron diffraction and neutron spectroscopy.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
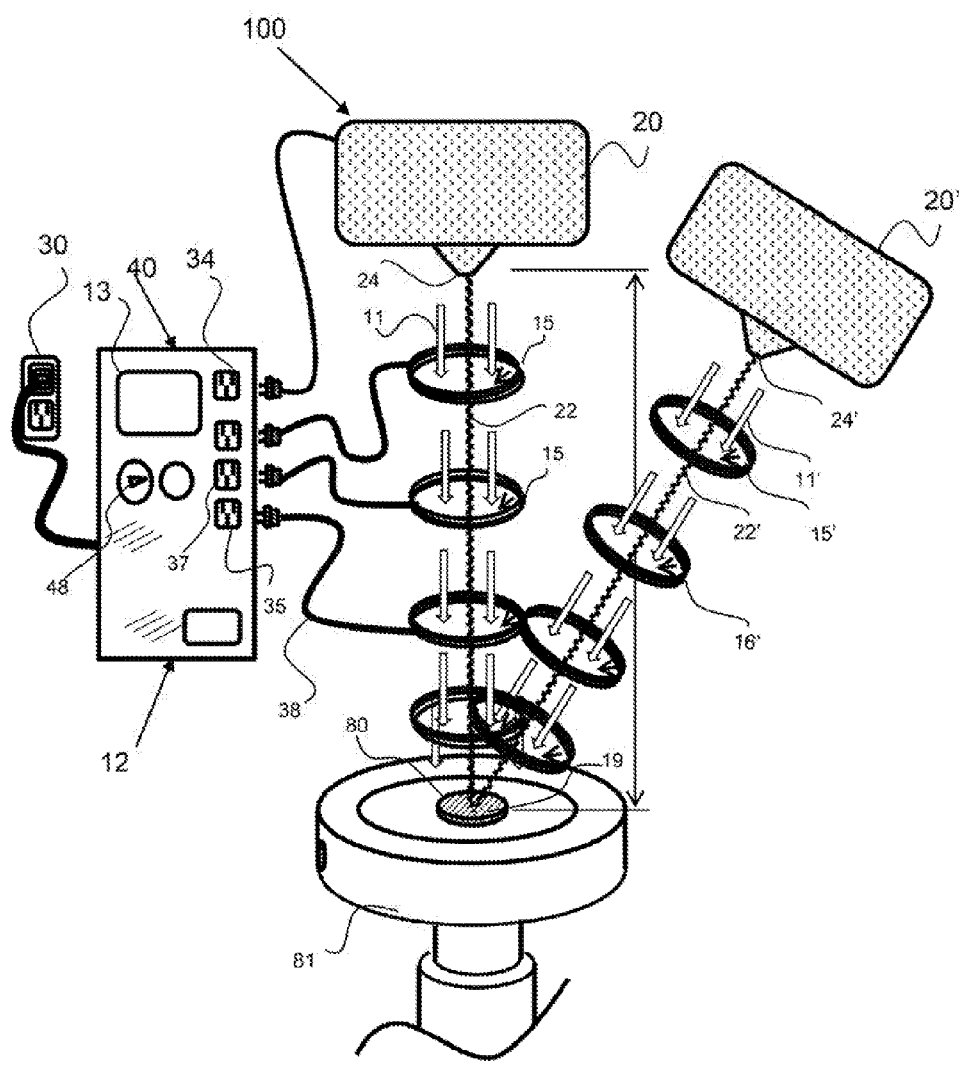

FIG. 1 shows a perspective view of an exemplary neutron beam diffraction material treatment system comprising a first and a second neutron beam source and neutron beams intersecting on a work-piece.

Figure 2:
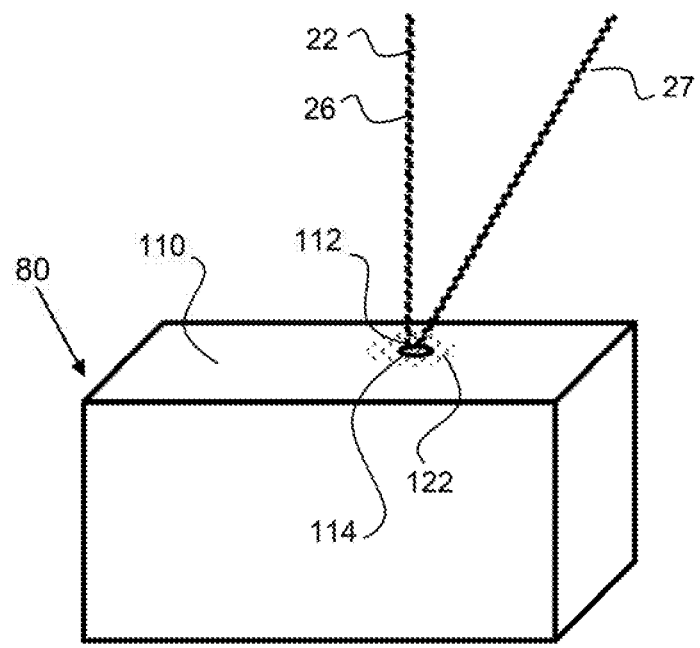

FIG. 2 shows a perspective view of an exemplary work-piece having first and a second neutron beams intersecting on the work-piece and creating neutron diffraction.

Figure 3:
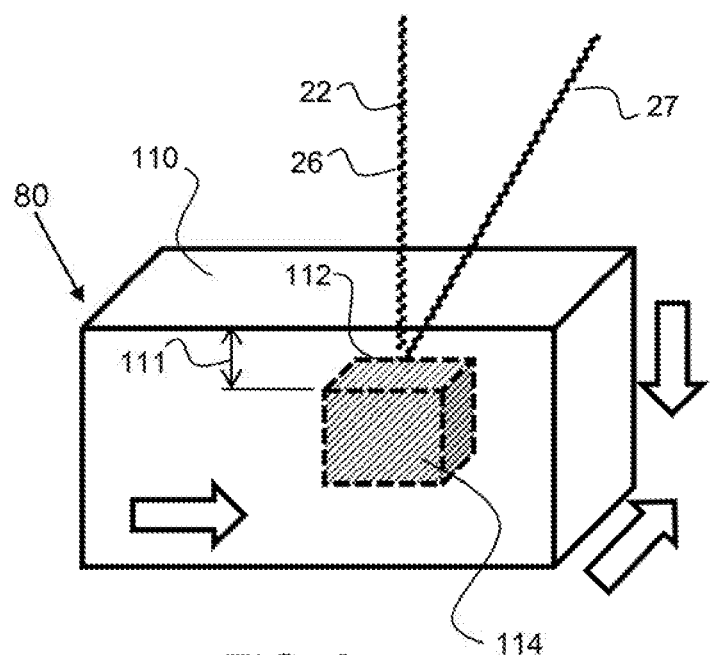

FIG. 3 shows a perspective view of an exemplary work-piece having first and second neutron beams intersecting within the interior of the work-piece and creating neutron diffraction. A discrete cube shaped treated work-piece portion has been created in the interior of the work-piece.

Figure 4:
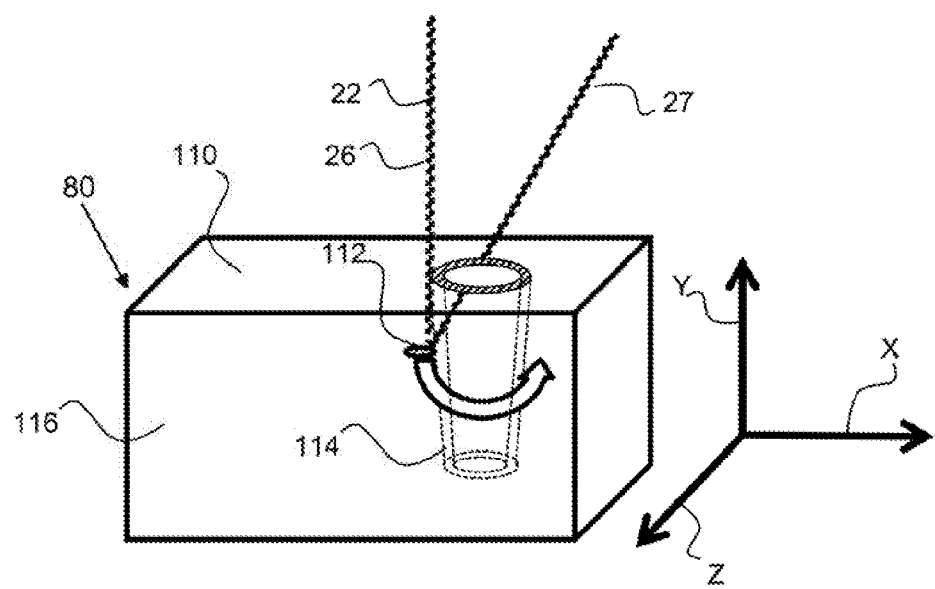

FIG. 4 shows a perspective view of an exemplary work-piece having first and second neutron beams intersecting within the interior of the work-piece and creating neutron diffraction. A discrete cylindrical shaped treated work-piece portion has been created in the interior of the work-piece.

Figure 5:
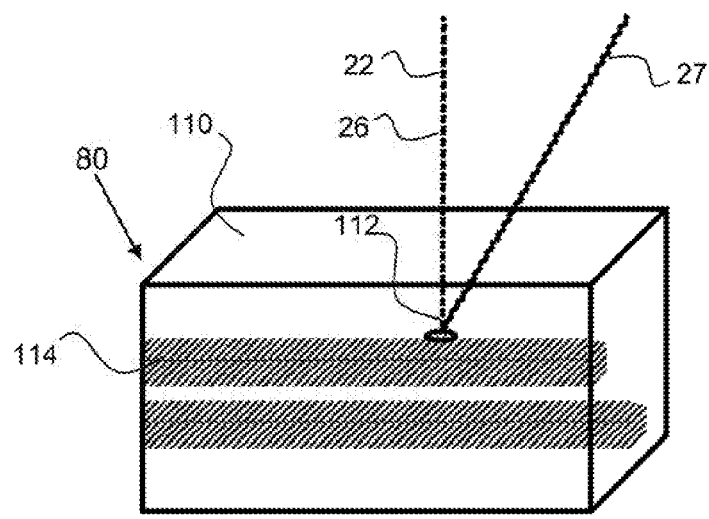

FIG. 5 shows a perspective view of an exemplary work-piece having first and second neutron beams intersecting within the interior of the work-piece and creating neutron diffraction. A beam shaped treated work-piece portion has been created in the interior of the work-piece.

FIG. 6 shows a perspective view of an exemplary work-piece having an I-Beam shaped treated work-piece portion.

FIG. 7 is a cross-sectional view along line 7-7 of FIG. 6 showing that the I-Beam shaped treated work-piece portion extends through the work-piece from Face A to Face B.

FIG. 8 shows a perspective view of an exemplary work-piece having a planar shaped treated work-piece portions.

FIG. 9 shows a cross-sectional view along line 9-9 of FIG. 8 showing that the planar shaped treated work-piece portion extends through the work-piece from Face A to Face B. The planar shaped treated work-piece portions form treated panel portions within the interior of the work-piece.

FIG. 10 shows a perspective view of an exemplary work-piece having a cylindrical shaped treated work-piece portions.

FIG. 11 shows a cross-sectional view along line 11-11 of FIG. 10 showing that the cylindrical shaped treated work-piece portion extends through the work-piece from Face A to Face B.

FIG. 12 shows a cross-sectional view along line 12-12 of FIG. 10 showing that the cylindrical shaped treated work-piece portion extends through the work-piece from Face A to Face B.

FIG. 13 shows a perspective view of an exemplary work-piece having a thread type treated work-piece portions.

FIG. 14 shows a cross-sectional view along line 14-14 of FIG. 13 showing that the thread type treated work-piece portion extend through the work-piece from and are configured within the interior volume of the work-piece.

FIG. 15 shows a cross-sectional view along line 15-15 of FIG. 13 showing that the thread type treated work-piece portions extend through the work-piece from surface to surface.

Figure 16:
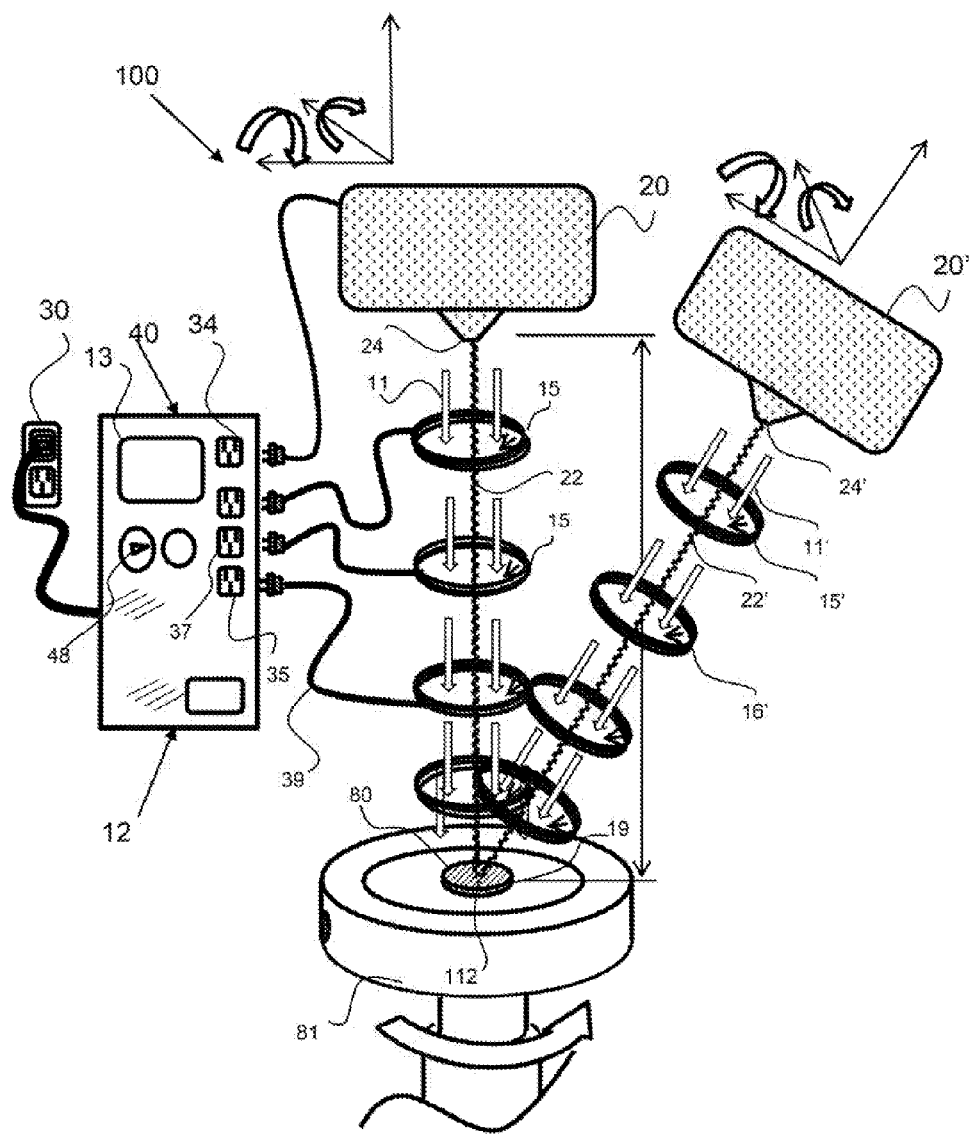

FIG. 16 shows a perspective view of an exemplary neutron beam diffraction material treatment system comprising a first neutron beam source and a second neutron beam source producing neutron beams that are intersecting on a work-piece 80.

Figure 17:
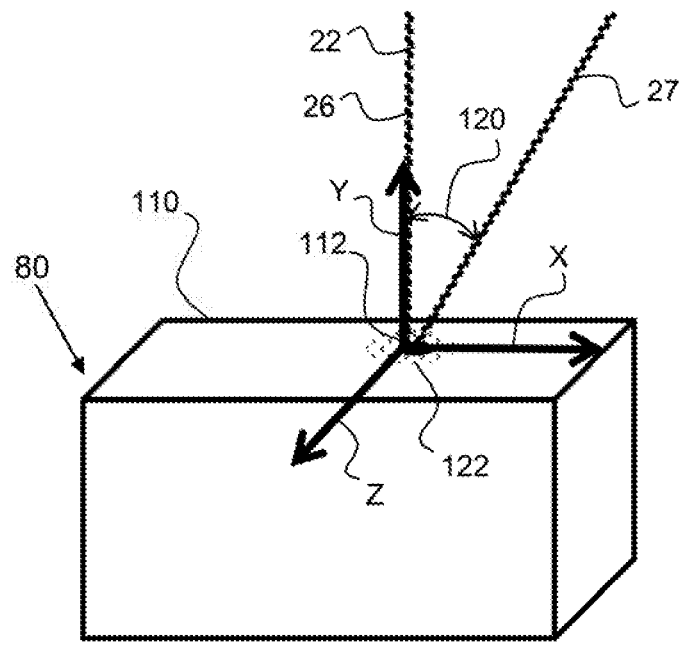

FIG. 17 shows a perspective view of a first neutron beam and a second neutron beam intersecting on a work-piece to create neutron diffraction and having an offset angle.

Figure 18:
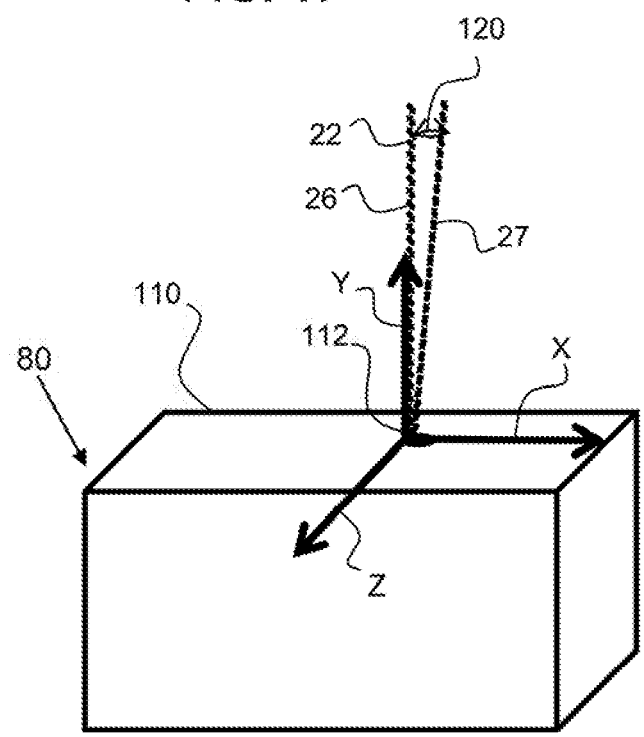

FIG. 18 shows a perspective view of a neutron beam and a second neutron beam intersecting on a work-piece to create neutron diffraction and having an offset angle. In this embodiment, the second neutron beam is at a much lower offset angle than the embodiment shown in FIG. 17.

Figure 19:
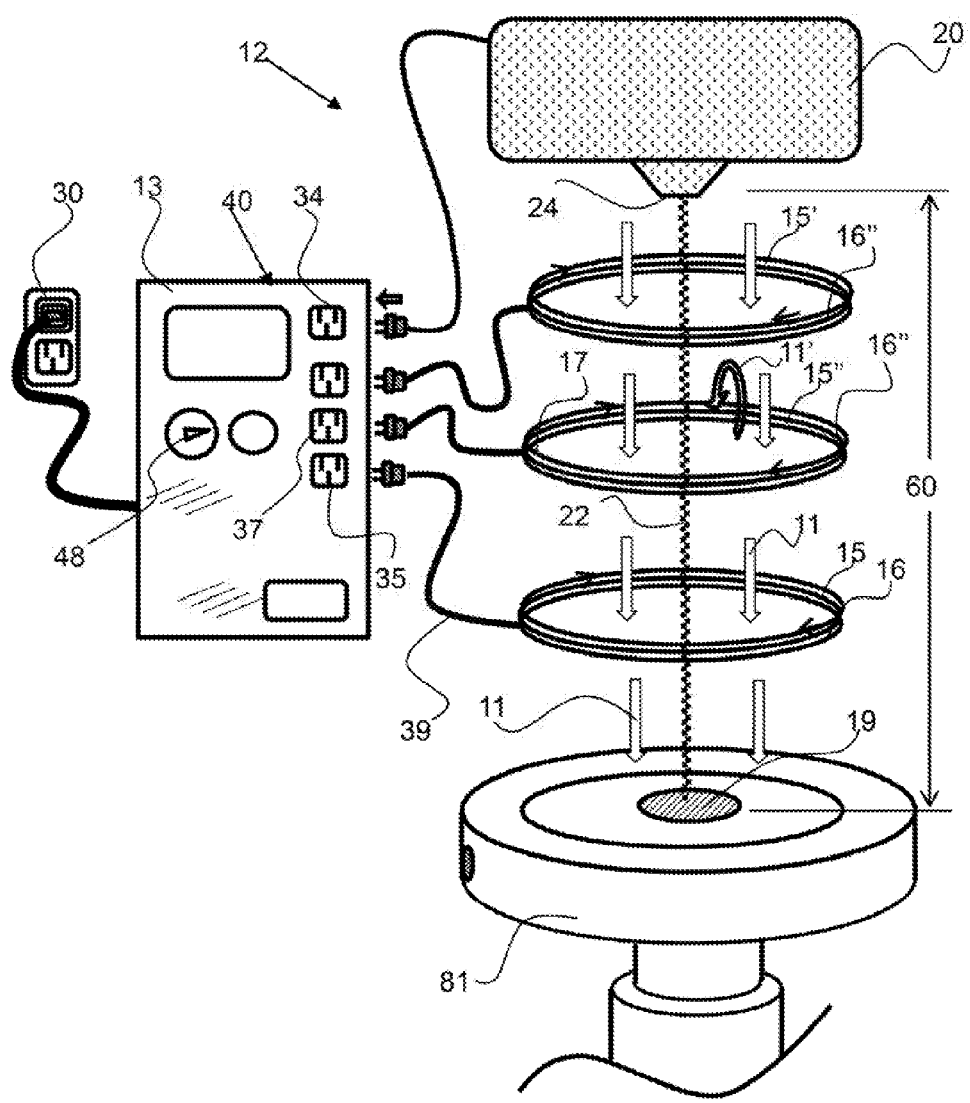

FIG. 19 shows a perspective view of an exemplary neutron beam regulator system comprising a power control system and a plurality of discrete magnetic coils configured around a neutron beam and extending substantially from the neutron beam source to the target, or the neutron beam length.

Figure 20:
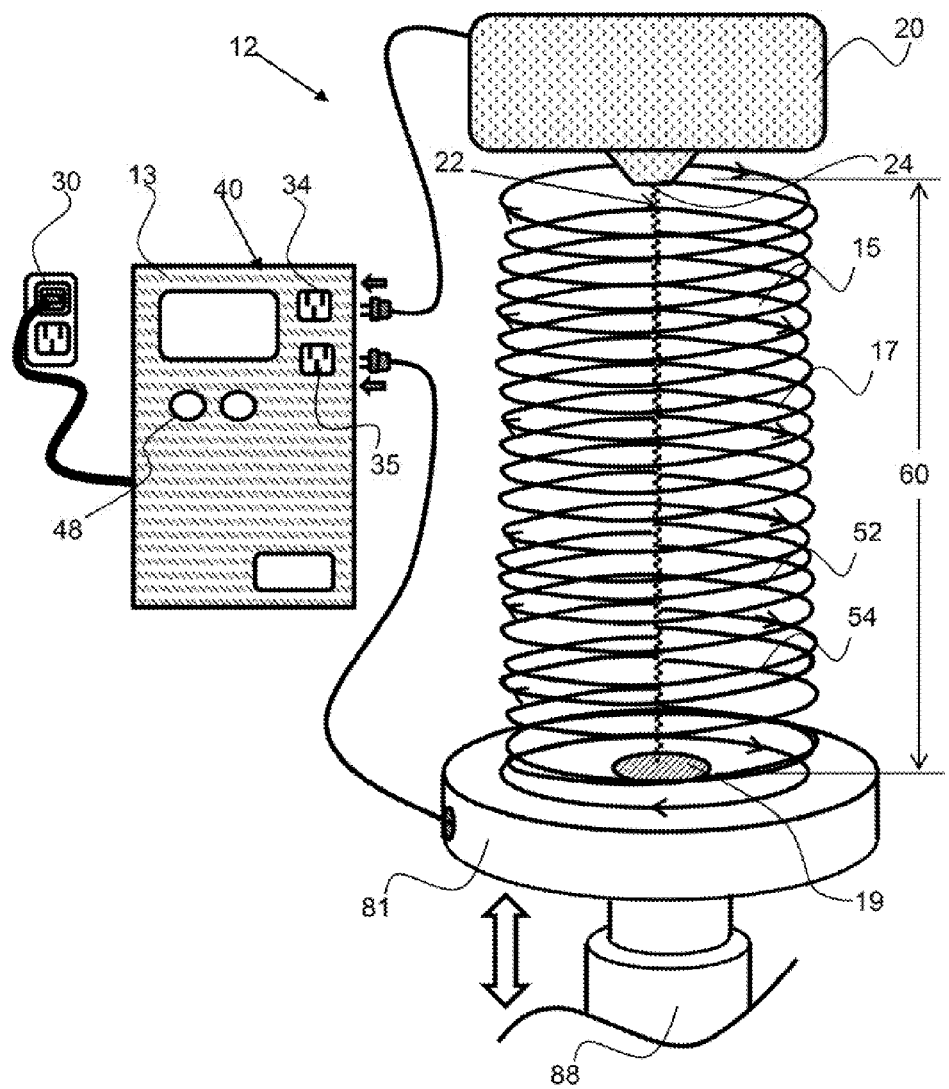

FIG. 20 shows a perspective view of an exemplary neutron beam regulator system comprising a continuous magnetic coil configured around a neutron beam and extending substantially the entire neutron beam length.

Figure 21:
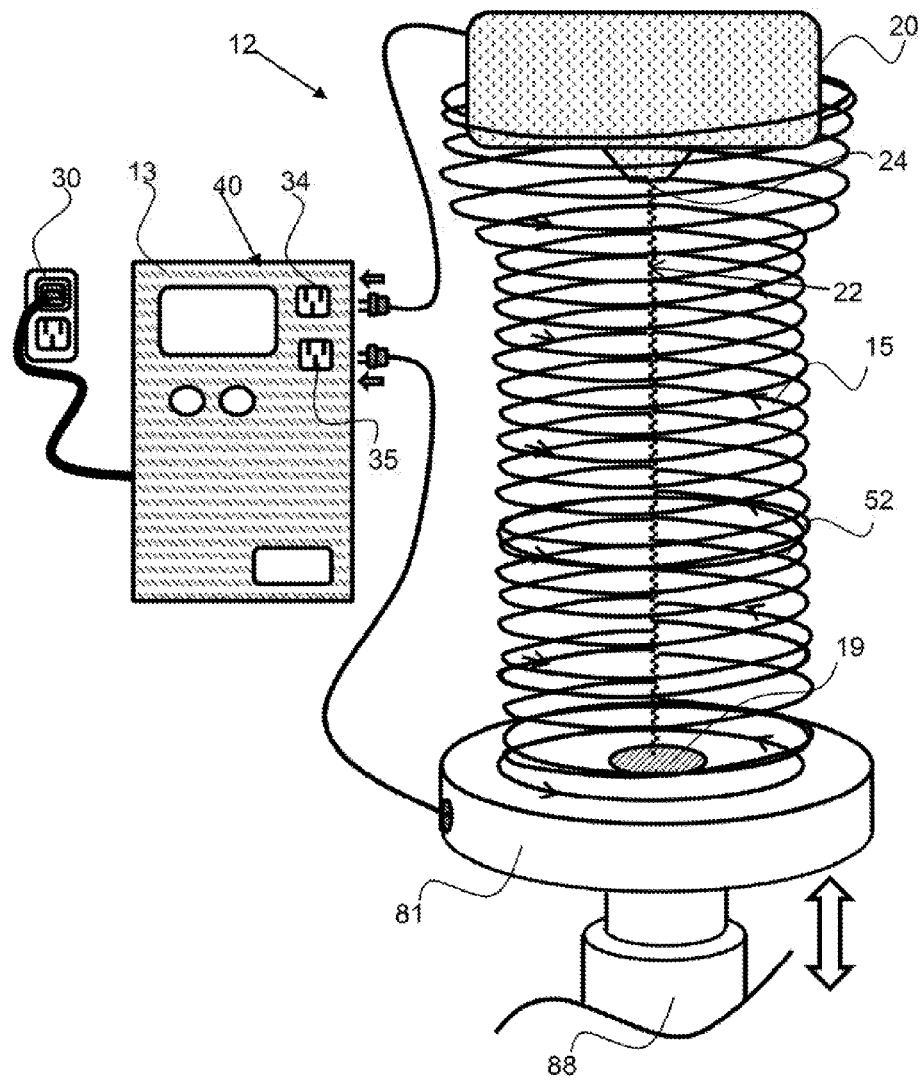

FIG. 21 shows a perspective view an exemplary neutron beam regulator system comprising a continuous magnetic coil configured partially around the neutron beam source or generator.

Figure 22:
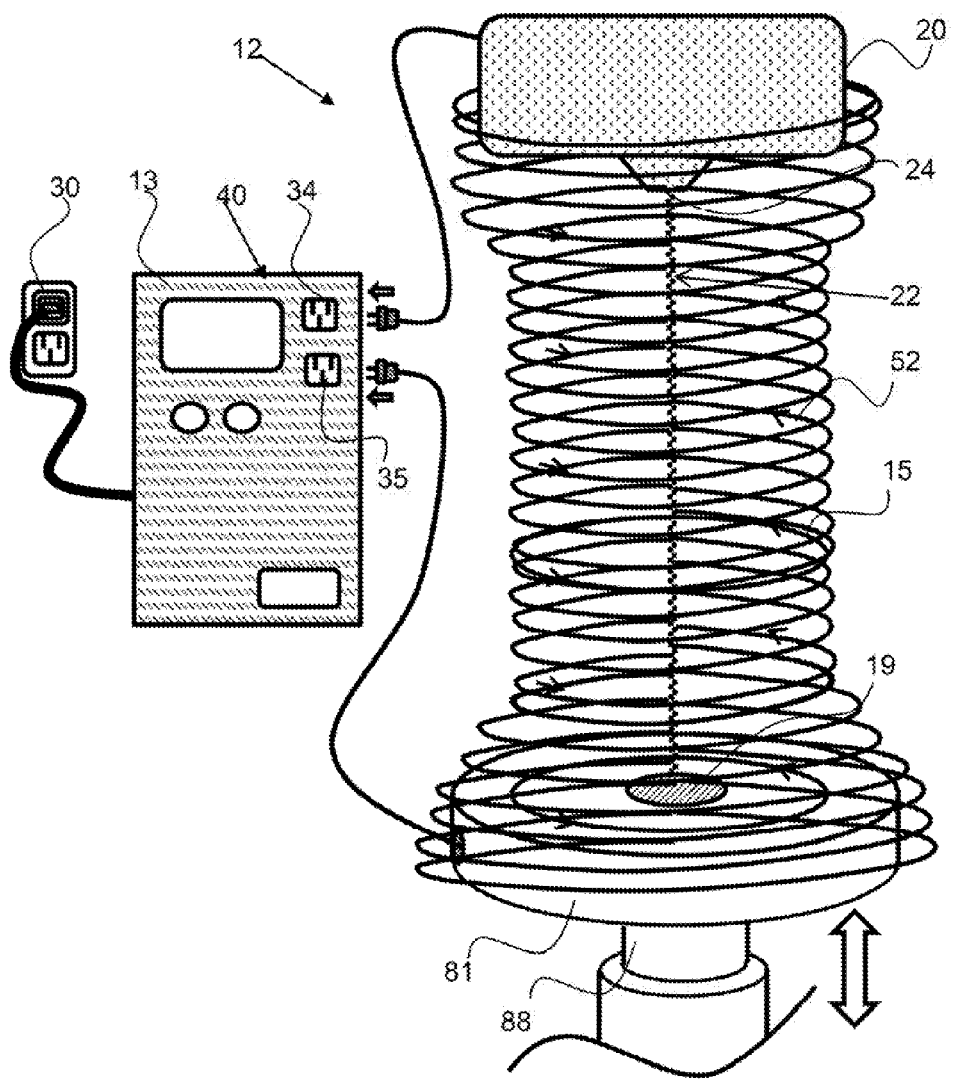

FIG. 22 shows a perspective view of an exemplary neutron beam regulator system comprising a continuous magnetic coil configured partially around the neutron beam source or generator and partially around a work-piece station.

Figure 23:
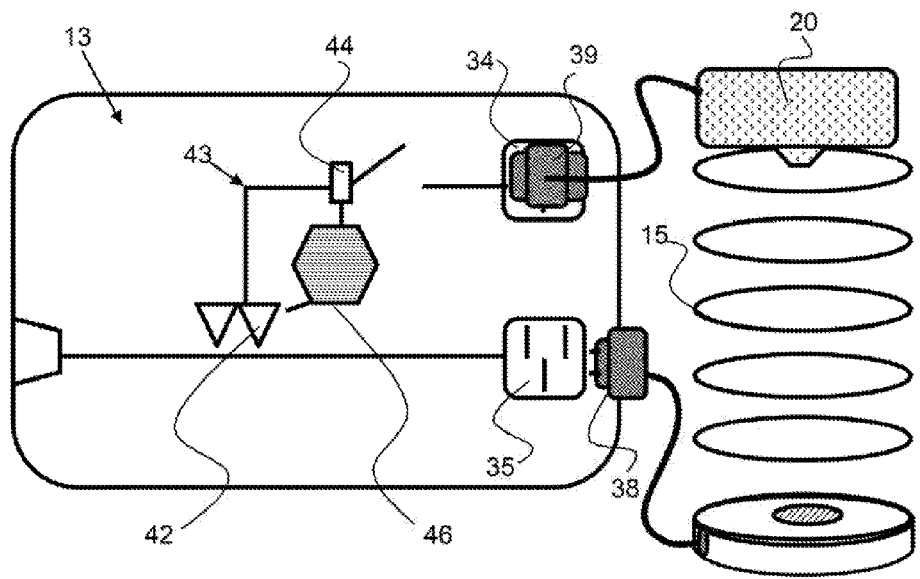

FIG. 23 shows a diagram of an exemplary power control system comprising a power safety feature configured to terminate power to a neutron beam source in the event that no power is being drawn by a containment magnetic coil. The switch is in an open position and the neutron beam source is deactivated.

Figure 24:
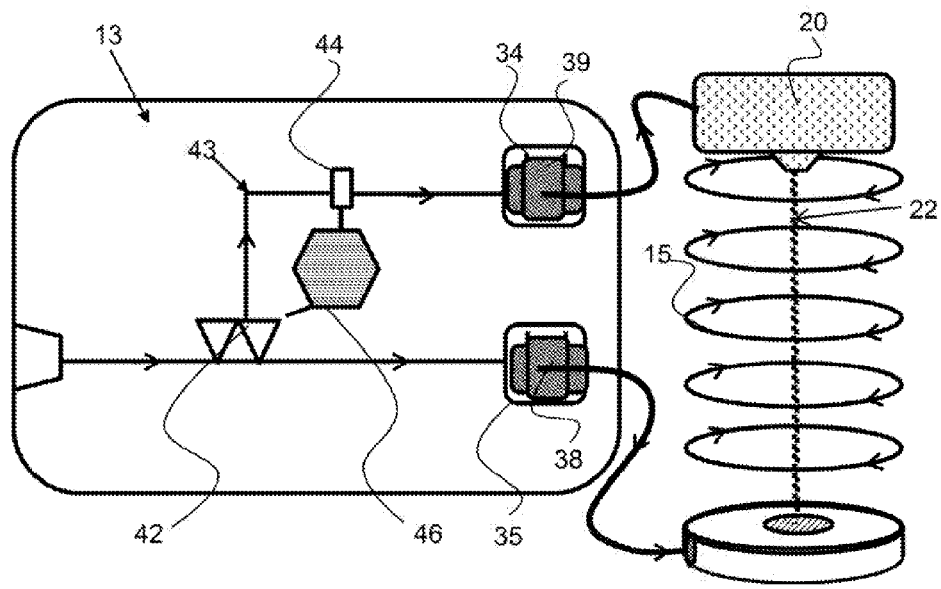

FIG. 24 shows a diagram of an exemplary power control system comprising a power safety feature configured to terminate power to a neutron beam source in the event that no power is being drawn by a containment magnetic coil. The switch is in a closed position and the neutron beam source is activated, as the magnetic coil is drawing power to contain the neutron beam.

Figure 25:
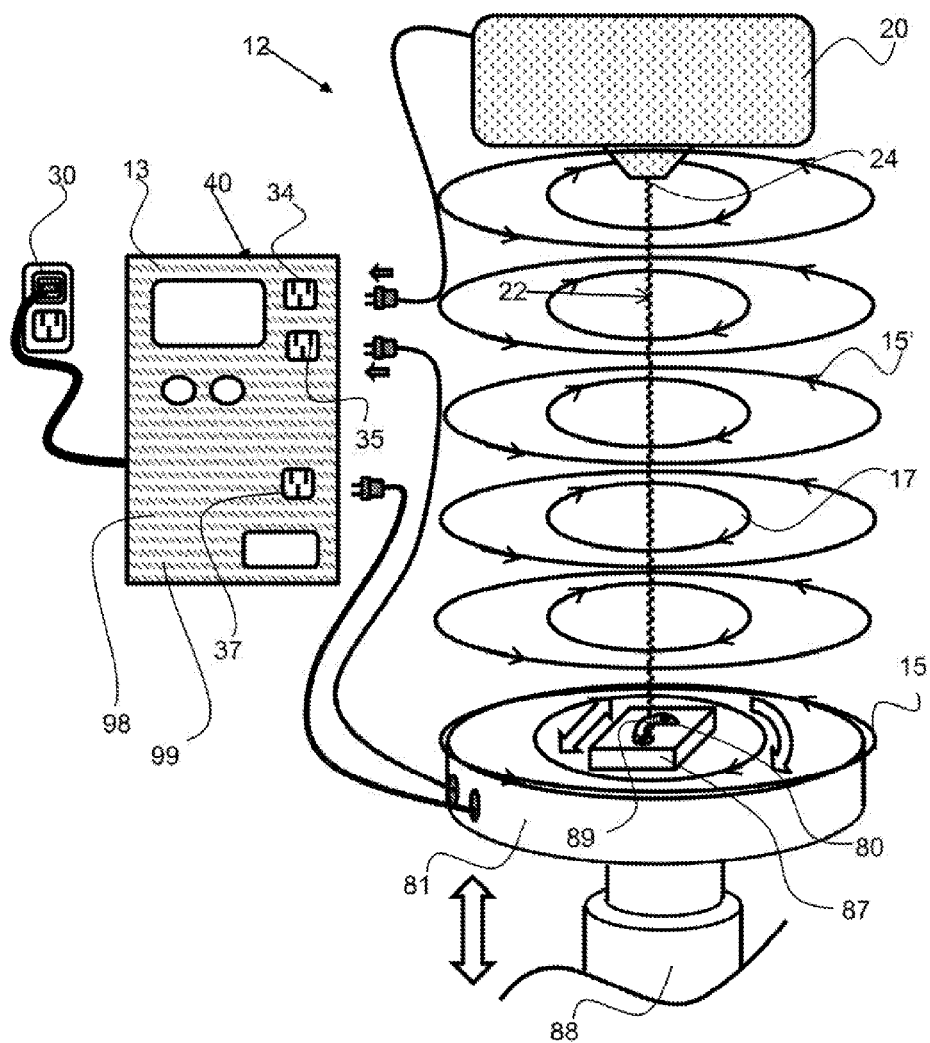

FIG. 25 shows a perspective view of an exemplary neutron beam regulator system comprising a containment magnetic coil configured around a modulating magnetic coil.

Figure 26:
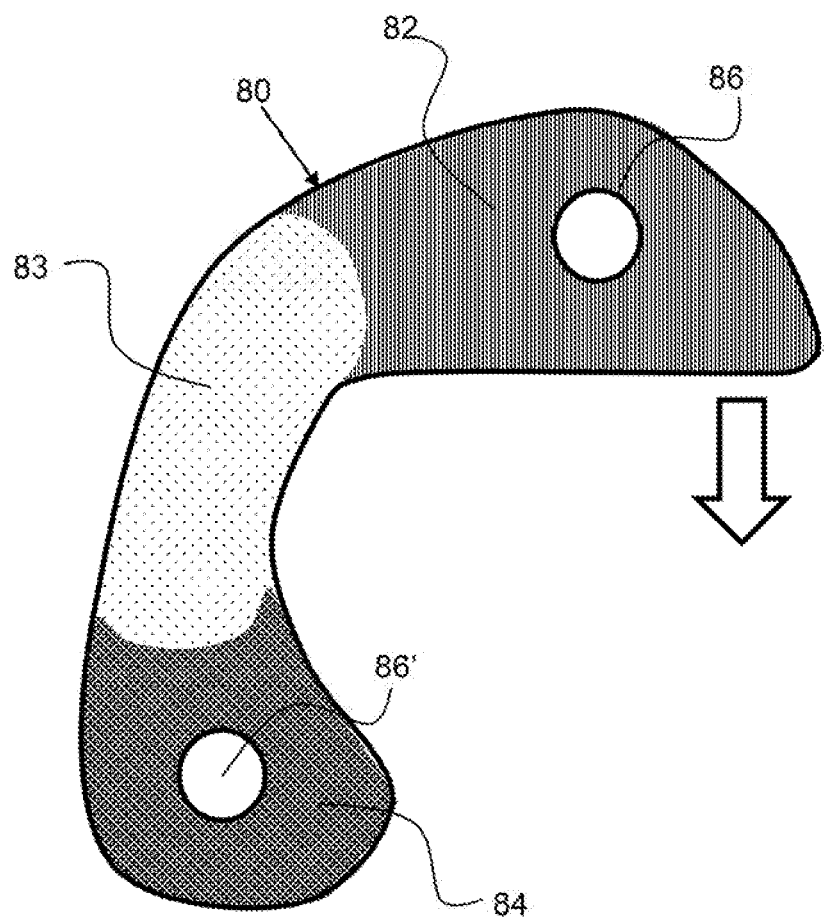

FIG. 26 shows a top-down view of a work-piece having areas treated with different levels of neutron bombardment through magnetic coil modulation.

Figure 27:
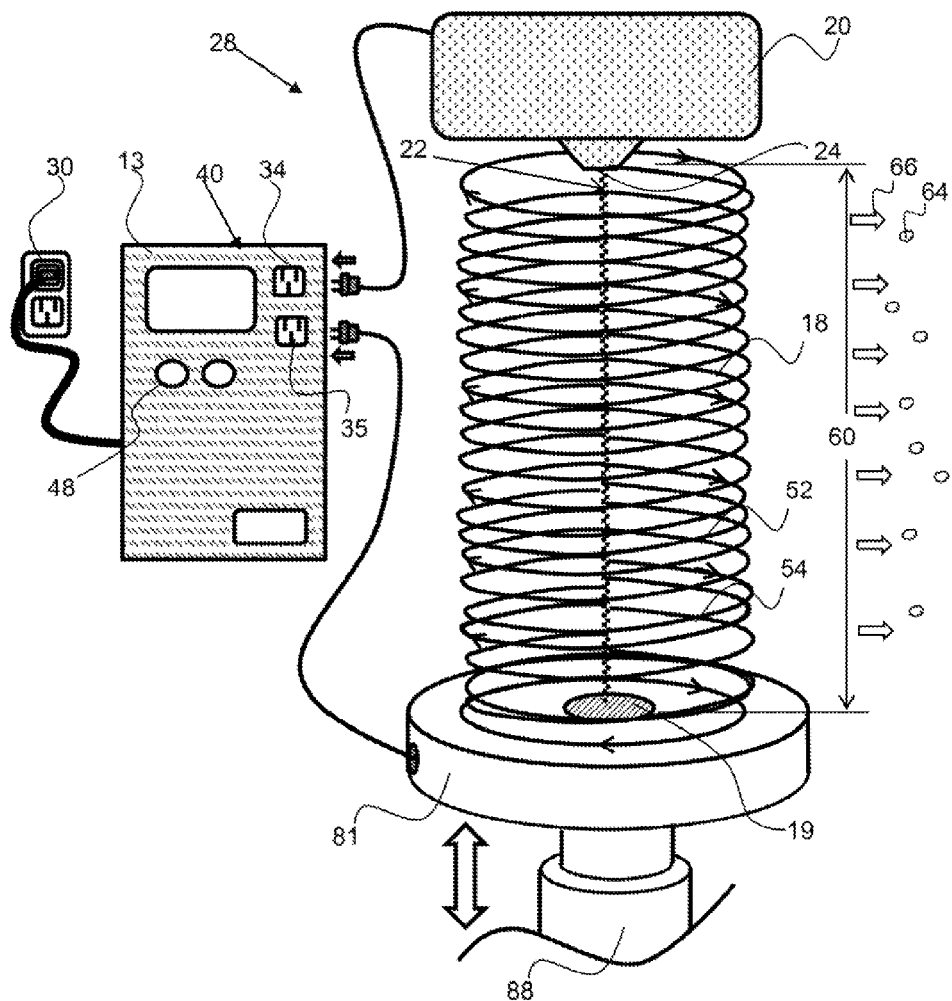

FIG. 27 shows a perspective view of an exemplary neutron beam system comprising a continuous excluding magnetic coil configured around a neutron beam and extending substantially the entire neutron beam length.

Figure 28:
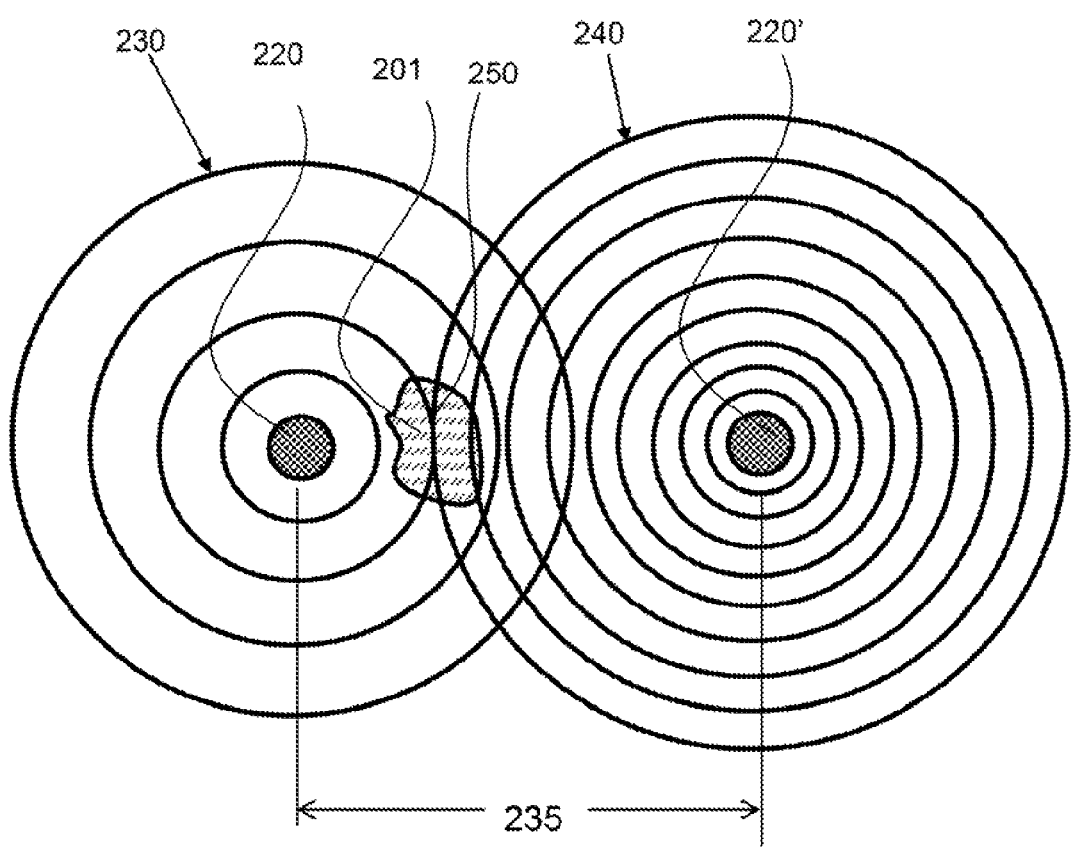

FIG. 28 shows coherence of two beams at a treatment location.

Figure 29:
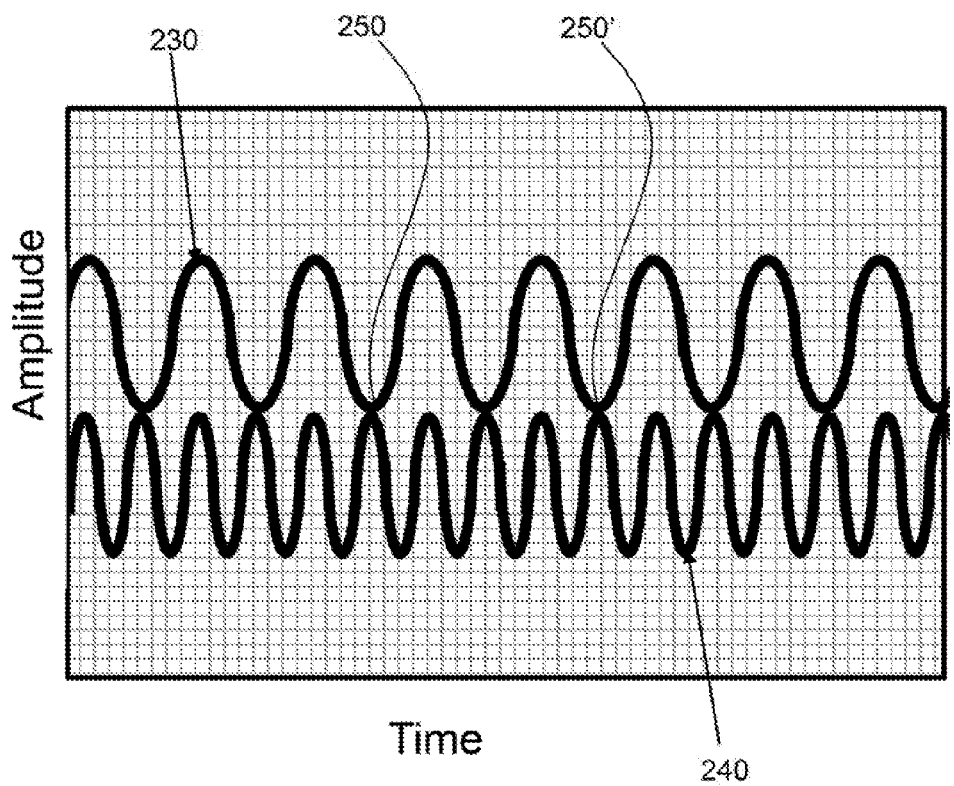

FIG. 29 shows a first beam having a first frequency and a second beam having a second frequency that is higher than the first beam frequency.

Figure 30:
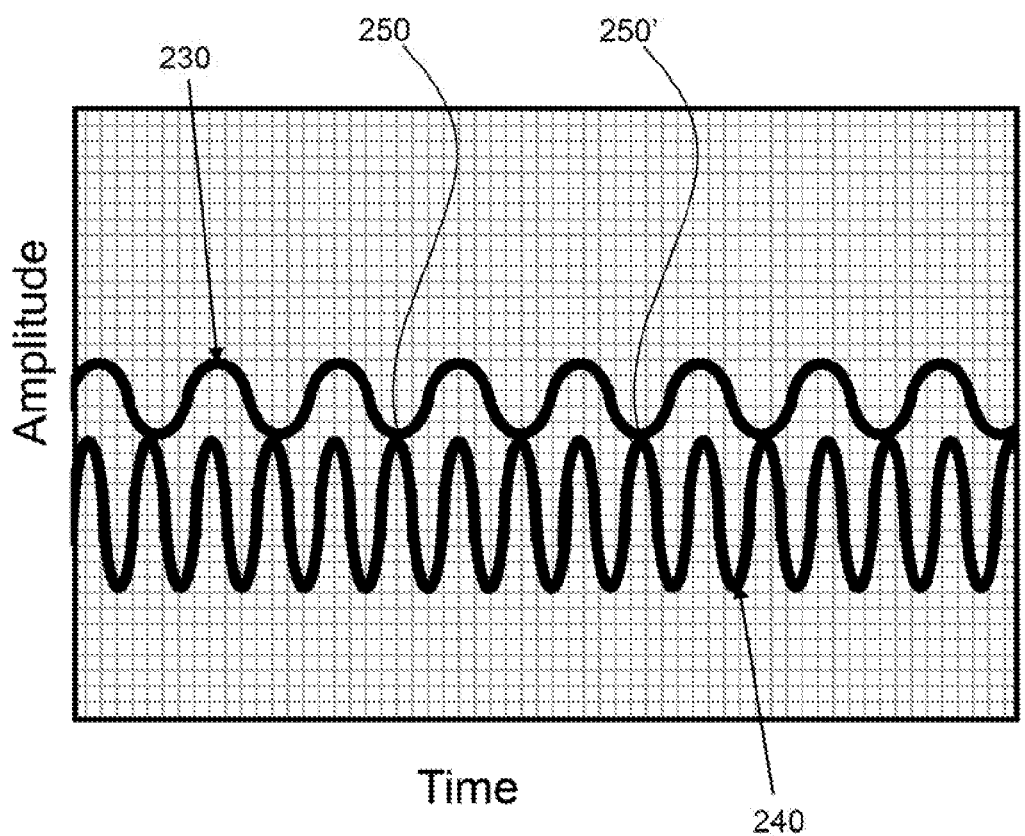

FIG. 30 shows a first beam having a first frequency and amplitude, and a second beam having a second frequency and amplitude.

Figure 31:
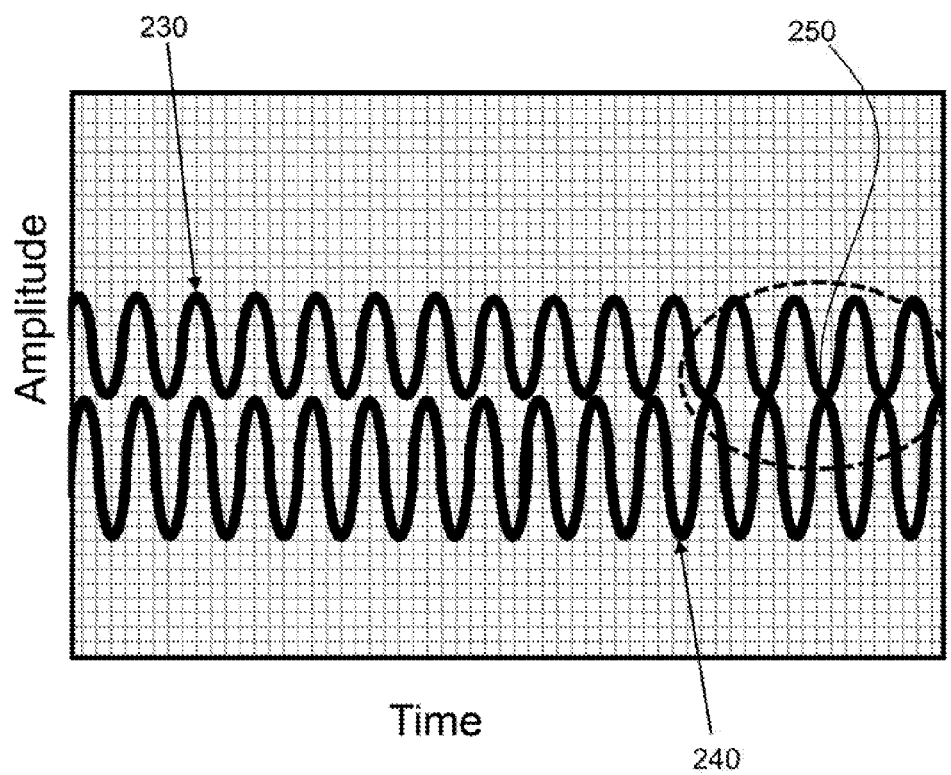

FIG. 31 shows a first beam and second beam having a coherence.

Figure 32:
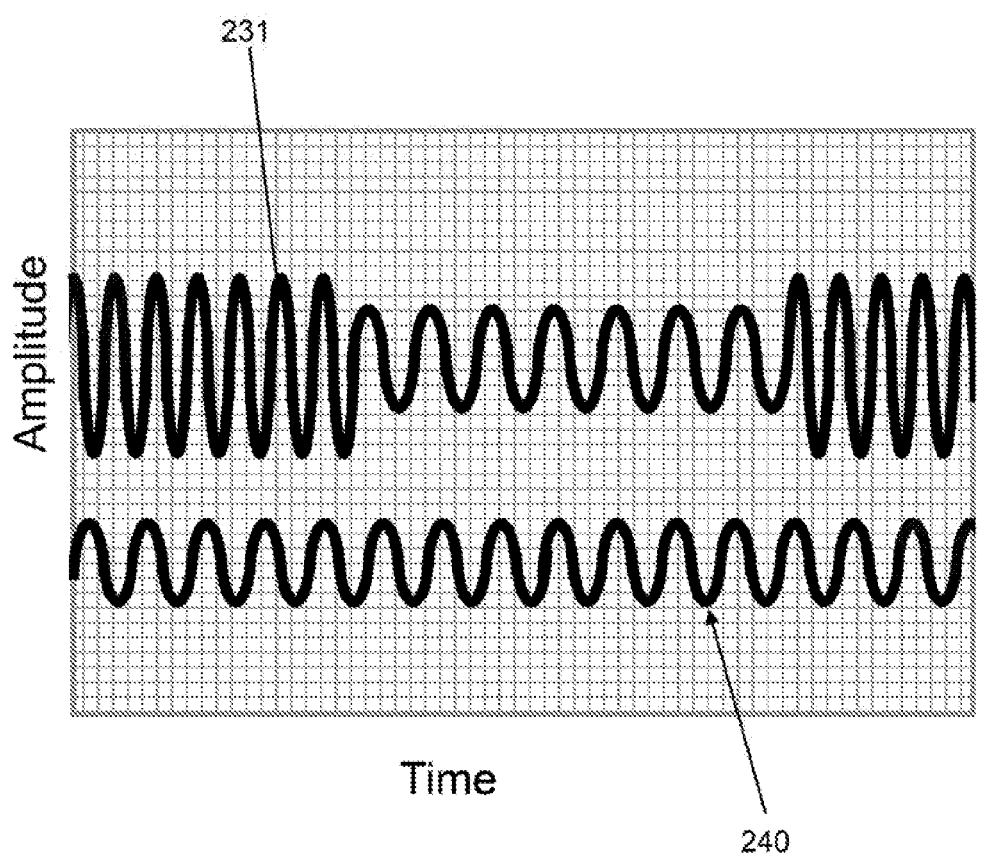

FIG. 32 shows a first complex beam or wave, wherein the frequency and amplitude change as a function of time.

Figure 33:
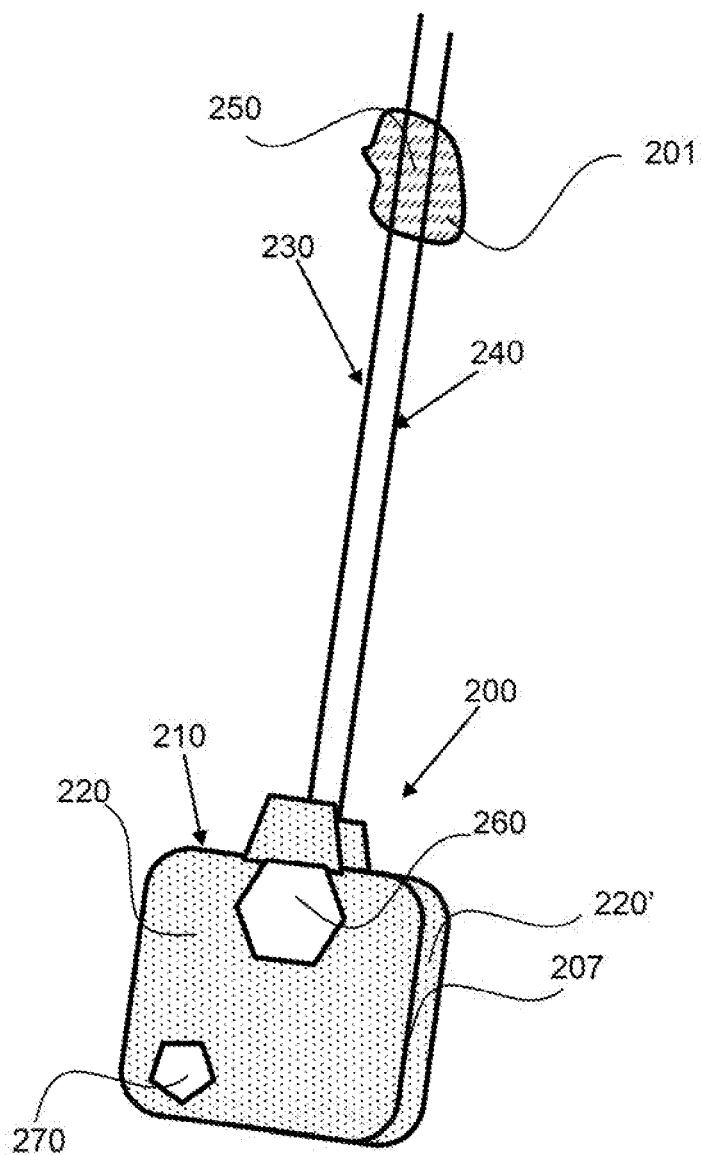

FIG. 33 shows a control system having first and second beam generators that produce a first and second beam, respectively.

Figure 34:
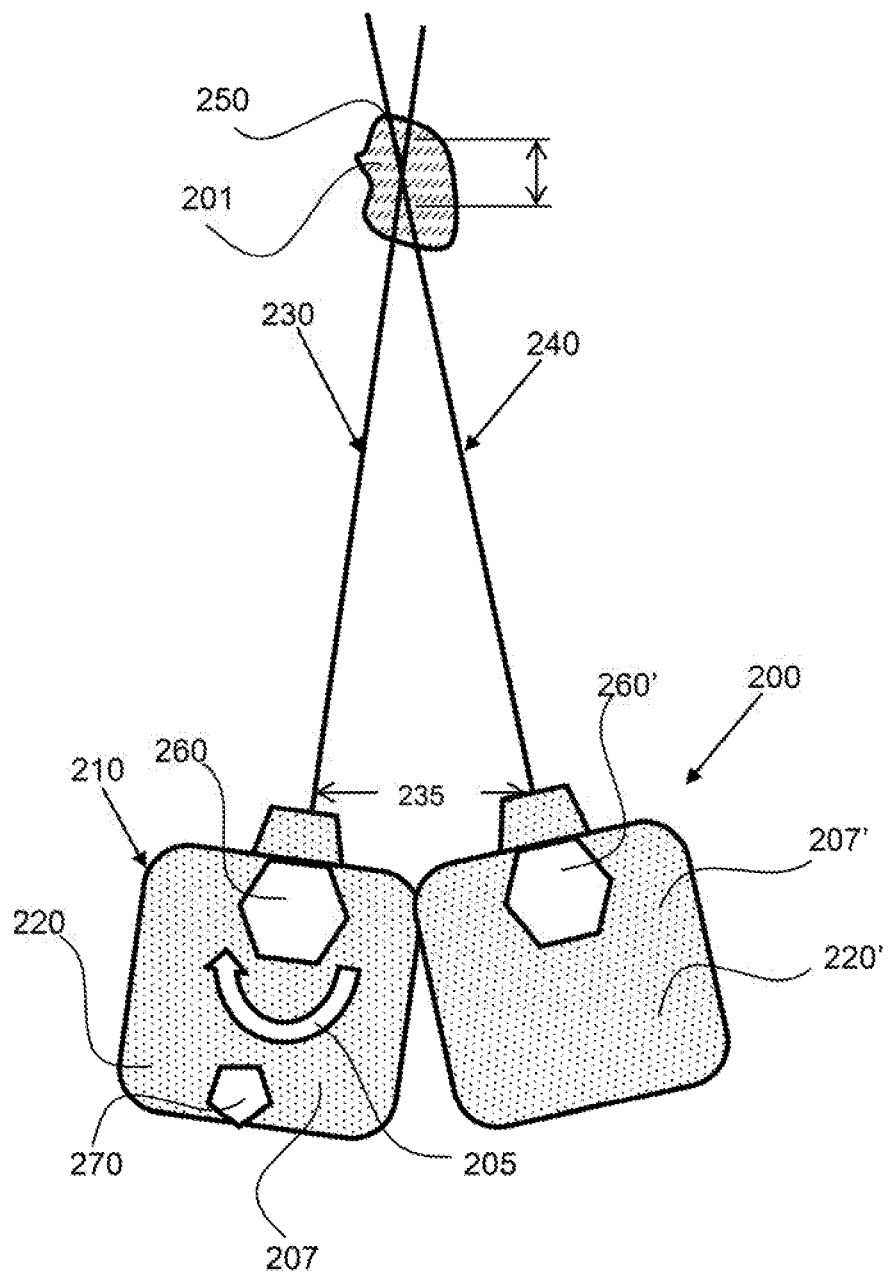

FIG. 34 shows a control system having first and second beam generators that are offset from each other and produce beams that intersect at a treatment location.

Figure 35:
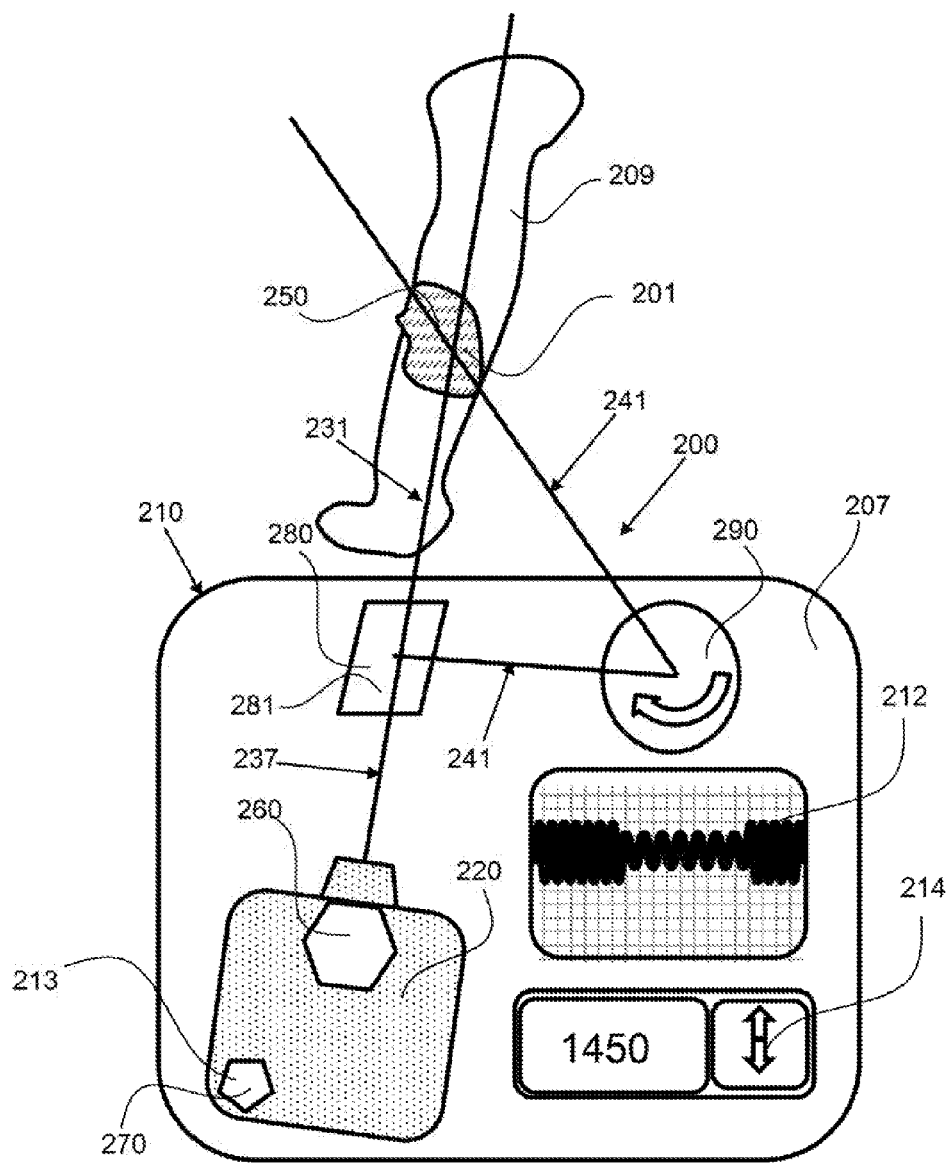

FIG. 35 shows a control system comprising a beam generator, a prism and mirror that produce a first and second beam that intersect at a treatment location.

Figure 36:
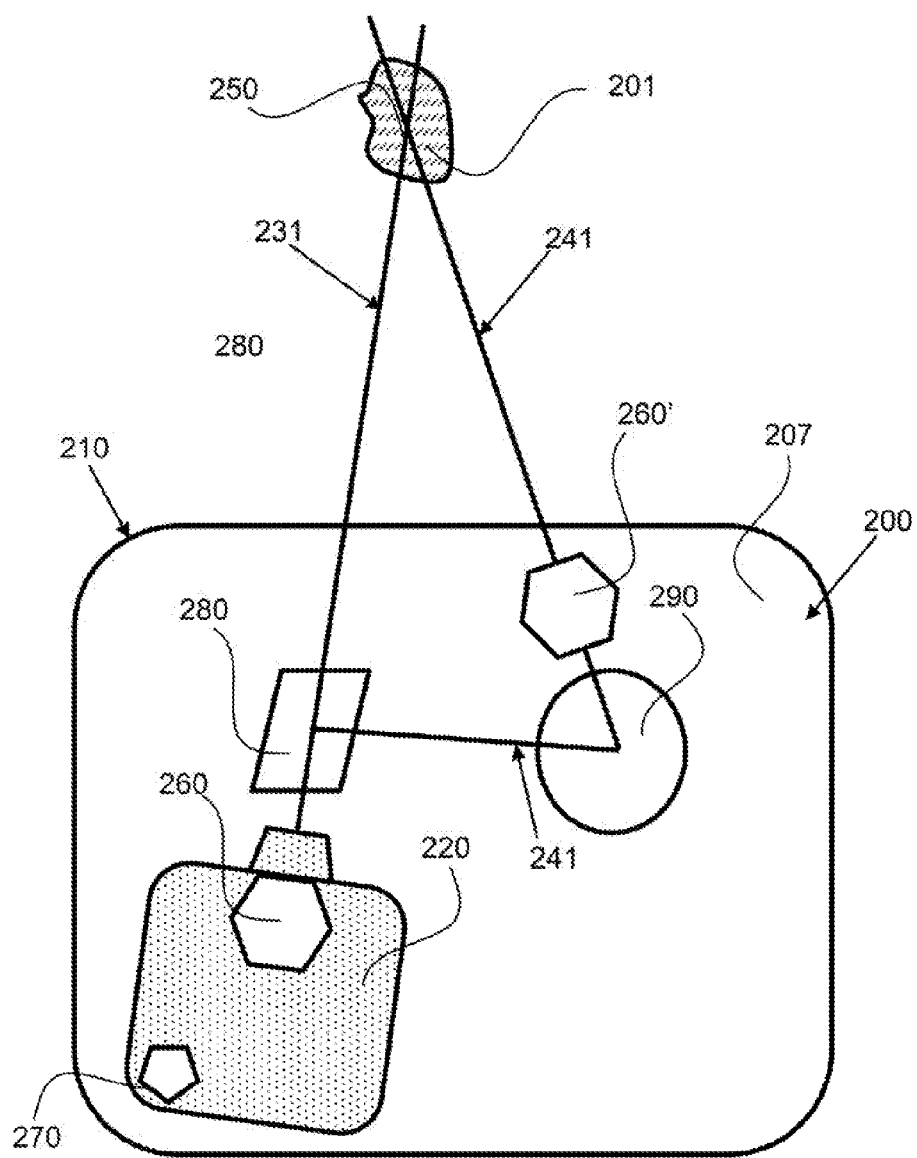

FIG. 36 shows a control system comprising a beam generator, a prism, a mirror and a second beam regulator for regulating the second beam.

Figure 37:
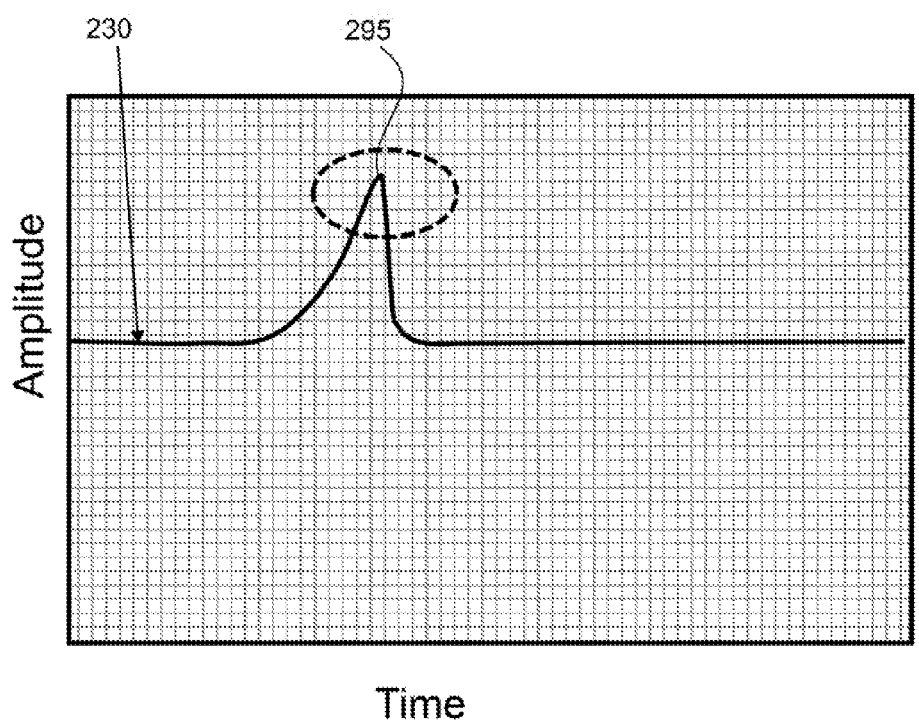

FIG. 37 shows a graph of a proton beam having a high energy frequency.

Figure 38:
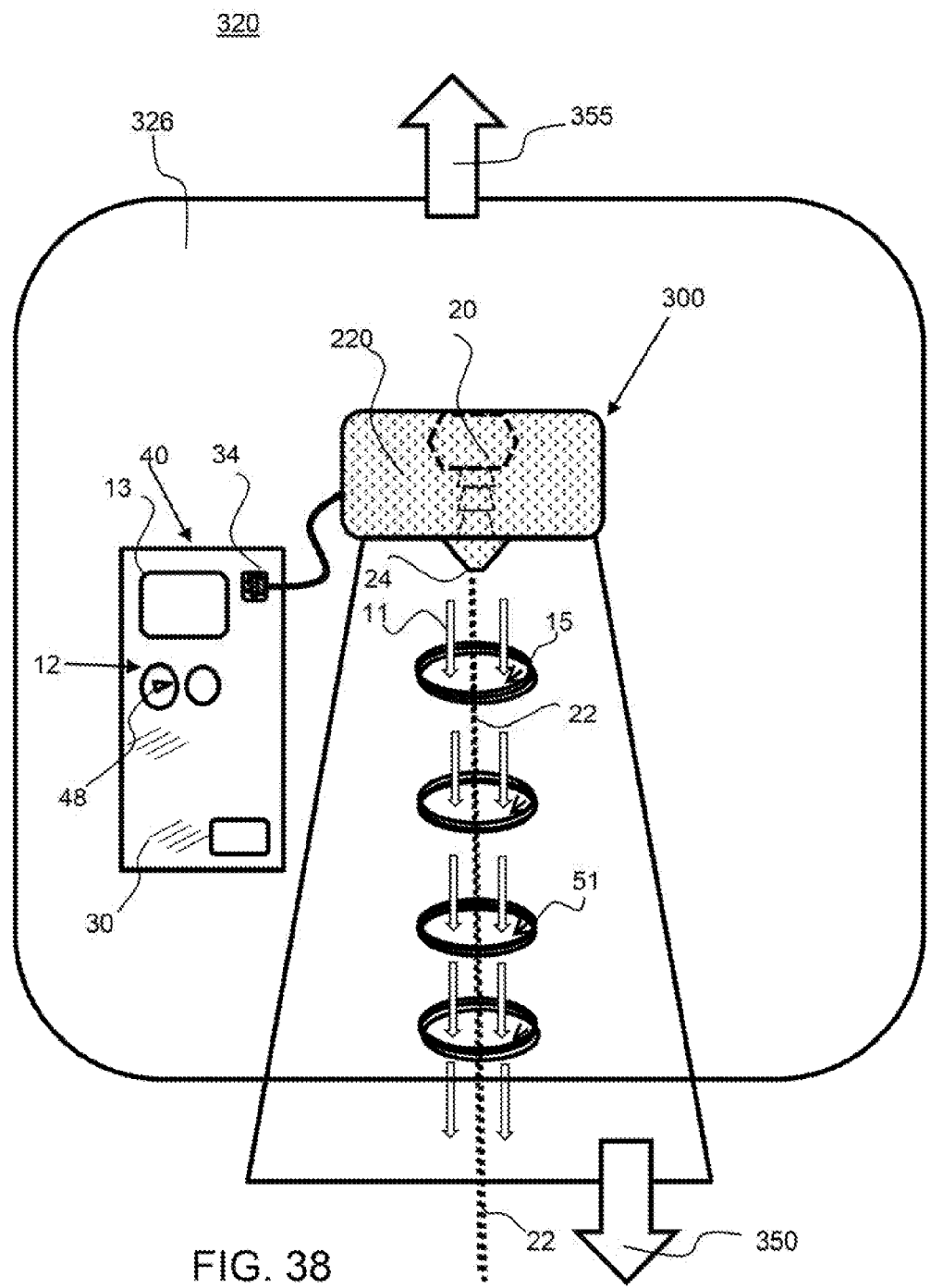

FIG. 38 shows an exemplary spacecraft having an exemplary neutron propulsion device comprising a neutron beam generator and neutron beam source as well as self-contained magnetic coils configured around the emitted neutron beam.

Figure 39:
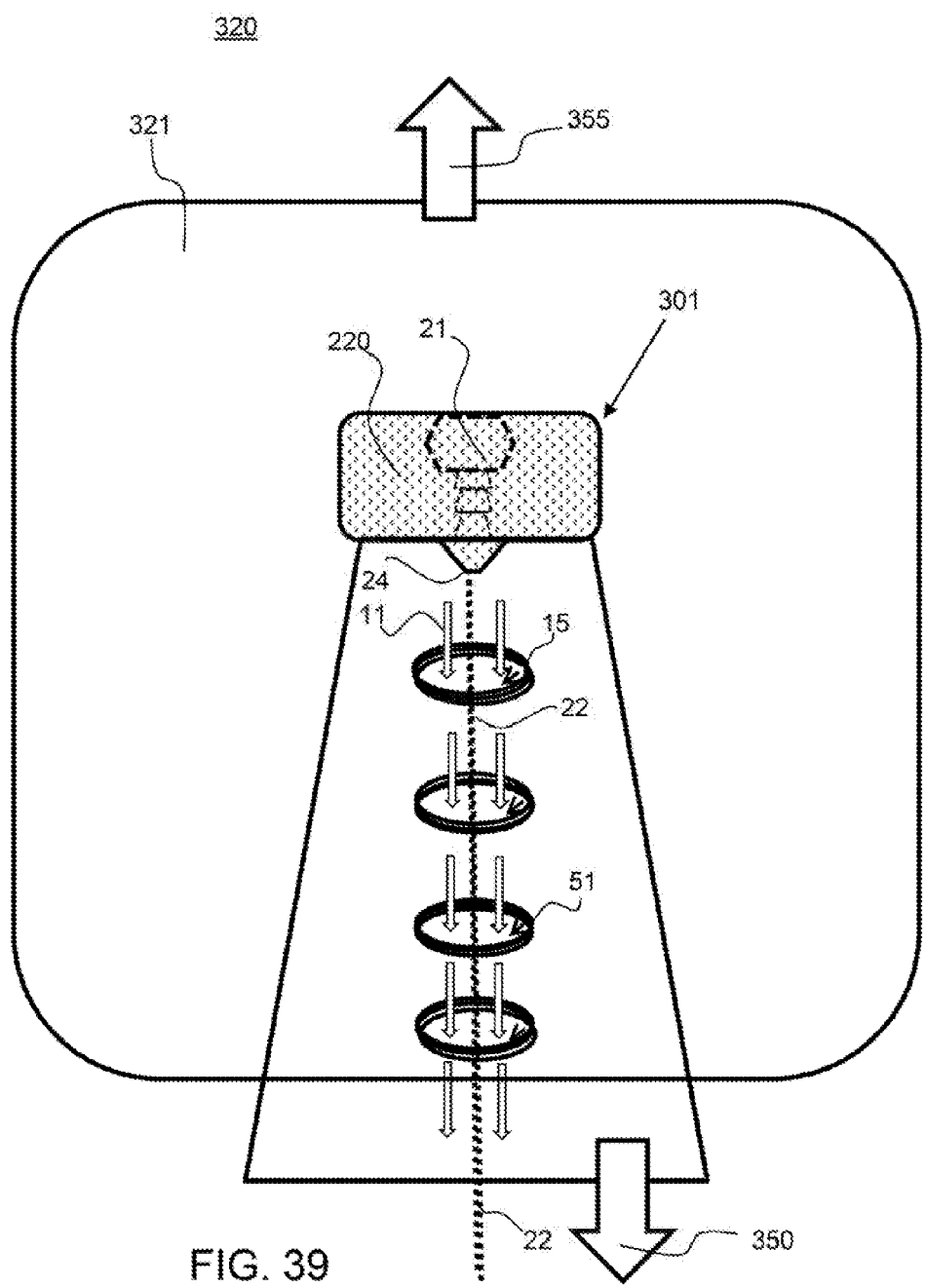

FIG. 39 shows an exemplary self-contained propulsion spacecraft having an exemplary self-contained neutron propulsion device comprising a neutron beam generator and self-contained neutron beam source as well as self-contained magnetic coils configured around the emitted neutron beam.

Figure 40:
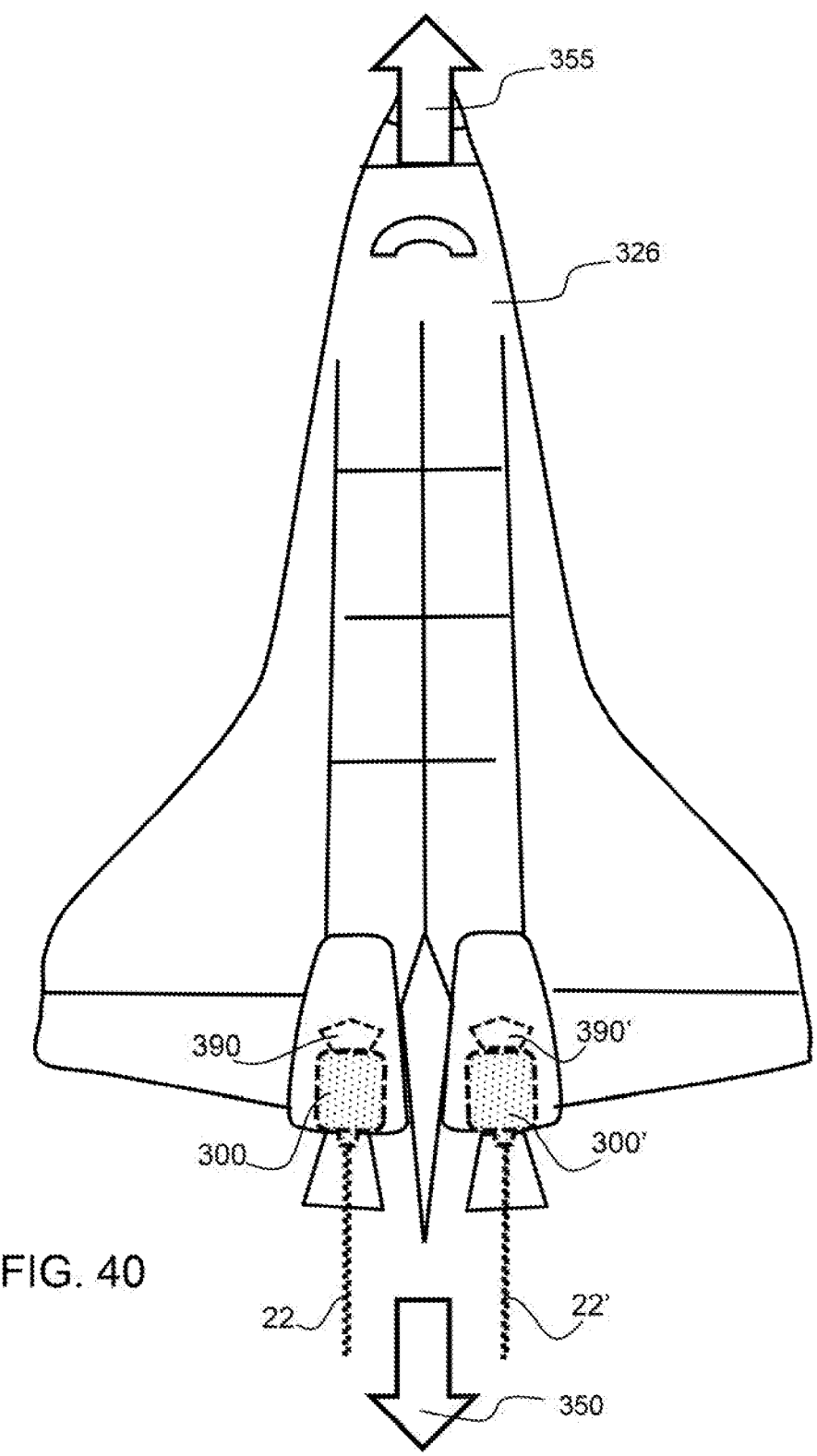
Figure 41:
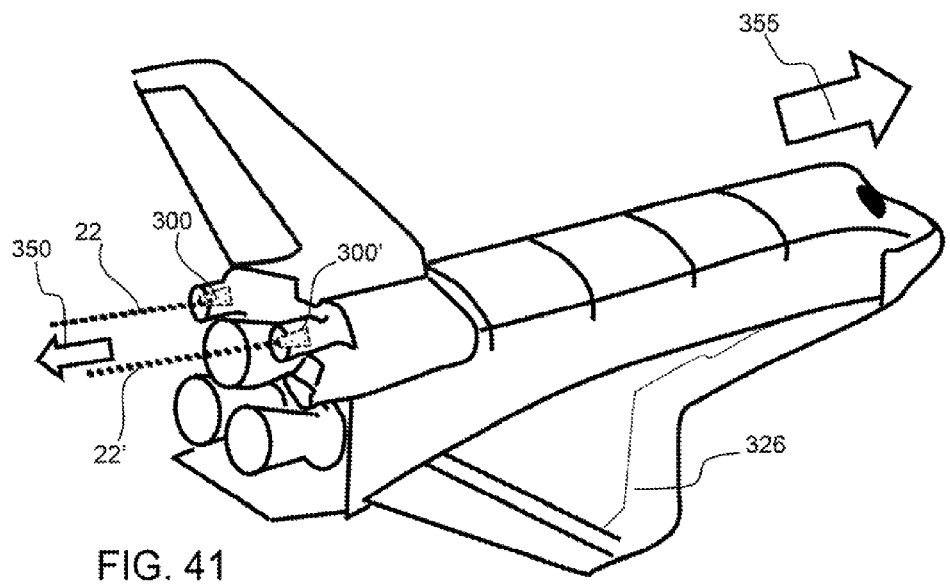

FIGS. 40 and 41 shows an exemplary spacecraft having a pair of neutron beam propulsion devices configured to propel and steer the spacecraft.

Figure 42:
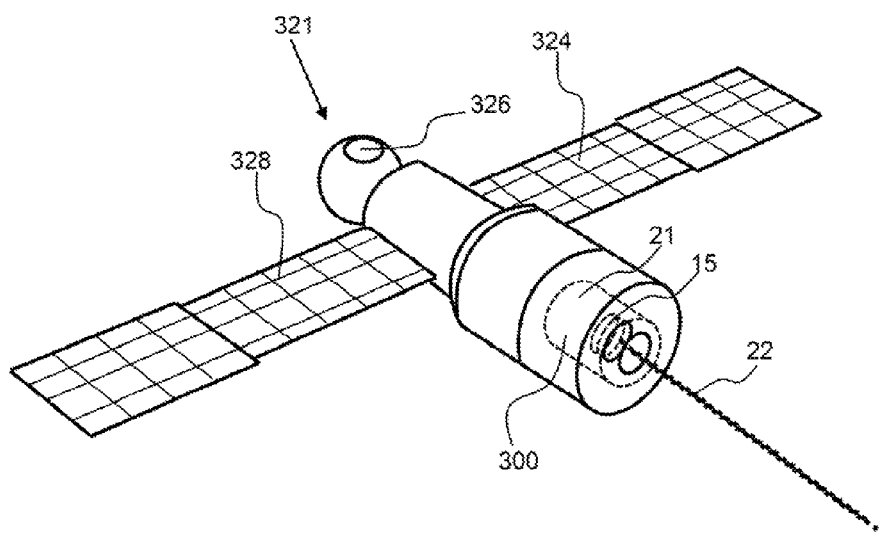

FIG. 42 shows an exemplary spacecraft having an exemplary neutron beam propulsion device.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications and improvements are within the scope of the present invention.

As shown in FIG. 1, an exemplary neutron beam diffraction material treatment system 100 comprises a first neutron beam source 20 and a second neutron beam source 20' that create neutron beams 22, 22' that are intersecting on a work-piece 80. The intersecting neutrons beams create neutron diffraction that produces a treatment portion within the work-piece, such as on the surface of the work-piece or within the depth of the work-piece. Also shown in FIG. 1 is a neutron beam regulator system 12, as described herein, that is coupled with the first neutron beam source. The neutron beam source may be used to contain the neutron or modulate the intensity of the neutron beam, as described herein. In this exemplary embodiment, the power control system 12 comprises a power control system 13, a power control system housing 40, at least one neutron beam source power supply output 34, a magnetic coil power supply output and a modulating coil output 37. It is to be understood that a single neutron beam regulator system may be coupled with both the first and second neutron beam sources or a separate neutron beam regulator system may be couple with each neutron beam source. In an alternative embodiment, magnetic coil extends around both the first and second neutron beams and may be controlled by a single regulator. It is also to be understood that two or more neutron beam sources and/or beams may be utilized in the neutron beam diffraction material treatment system, as described herein. The magnetic coils 15 shown in FIG. 1 are discrete magnetic coils and have a separate power supply, via separate magnetic coil plugs 38, to the power control system. The work-piece 80 is configured on a work-piece station 81 that may be configured to move in one or more direction and/or rotate.

As shown in FIG. 2, an exemplary work-piece 80 is being treated with the neutron beam diffraction material treatment system, as described herein. A first neutron beam 26 and a second neutron beam 27 are intersecting on the work-piece at an intersecting point 112 which creates neutron diffraction 122. The intersection of the two neutron beams and the neutron diffraction treats the work-piece material to produce a treated work-piece portion 114. A treated work-piece portion may be subjected to an elevated temperature and/or the entrapment of neutrons from the intersection of the two neutron beams. The treated work-piece portion in this embodiment is on the surface of the work-piece.

As shown in FIG. 3, an exemplary work-piece 80 is being treated with the neutron beam diffraction material treatment system, as described herein. The first and second neutron beams 26, 27, respectively, are intersecting within the depth of the work-piece, or below a work-piece surface 110. The depth 111 of the intersecting point 112 from the work-piece surface 111 may be any suitable depth and may be dynamically changed to produce various shapes and geometries of treated work-piece portions. As shown in FIG. 3 a cube shaped treated work-piece portion 114 has been created below the work-piece surface. The treated work-piece portion 114 is indicated by the cross-hashed cube within work-piece and is a bulk treated work-piece portion, as it does extend to a work-piece surface 110. In addition, the treated work-piece portion is a discrete work-piece portion having a defined outer surface that is not connected with another treated work-piece portion.

As shown in FIG. 4, an exemplary work-piece 80 is being treated with the neutron beam diffraction material treatment system, as described herein. A cylindrical shaped treated work-piece portion is being created by the movement of the intersecting point 112, as indicated by the bold arrow. A large portion of the work-piece is a non-treated work-piece portion 116. Both of the neutron beams are actuated in coordinated actuation, such that the intersecting point moves along the cylindrical shape to produce the cylindrically shaped treated work-piece portion. The neutron beams may be actuated in any suitable manner, such as along one or more axes, or rotated about any axis, such as a traditional X, Y, and Z axis configuration as shown. This cylindrical treated work-piece portion may be configured to reinforce a coupling or fastener that in attached or inserted into the work-piece 80. For example, a pin or a bolt may be configured for insertion into a cylindrically shaped treated work-piece portion. Treatment of the work-piece, as shown may reduce any wear associated with forces exerted on the pin or fastener, or may strengthen the attachment of the pin or fastener.

As shown in FIG. 5 an exemplary work-piece 80 is being treated with the neutron beam diffraction material treatment system, as described herein. Two elongated square shaped treated work-piece portions 114 have been produced, as indicated by the cross-hashed areas. Linear or elongated treated work-piece portions may strengthen the work-piece primarily in one direction, whereby the work-piece has a higher stiffness or break strength in the axis of the elongated treated work-piece portions, for example.

As shown in FIG. 6, an exemplary work-piece 80 has been treated with the neutron beam diffraction material treatment system, as described herein, to produce an exemplary I-beam shaped treated work-piece portion 114. The I-beam shaped portion has two planar portions that are parallel and in this example extend along the outer surface 110 of work-piece and a connecting portion that extends through the bulk or depth of the work-piece between the two planar portions. An I-beam shape is well known for providing a stiff structural member with reduced weight. As shown in FIG. 7 the I-beam shaped treated work-piece portion extends through the work-piece from Face A to Face B.

As shown in FIG. 8, an exemplary work-piece 80 has been treated with the neutron beam diffraction material treatment system, as described herein, to produce a plurality of planar shaped treated work-piece portions 114 with non-treated work-piece portion 116, therebetween. The planar shaped treated work-piece portions are substantially parallel and extend from a first surface 110 to a second surface 110' of the work-piece material. As shown in FIG. 9, the planar shaped treated work-piece portion extends through the work-piece from Face A to Face B. The planar shaped treated work-piece portions form treated panel portions within the interior of the work-piece.

As shown in FIG. 10, an exemplary work-piece 80 has been treated with the neutron beam diffraction material treatment system, as described herein, to produce a cylindrical shaped treated work-piece portion 114 around as aperture 115. As shown in FIG. 11, the cylindrical shaped treated work-piece portion extends through the work-piece from Face A to Face B. As shown in FIG. 12, the cylindrical shaped treated work-piece portion extends around the aperture 115.

As shown in FIG. 13 an exemplary work-piece has a thread type treated work-piece portions 132. FIG. 14 shows a cross-sectional view along line 14-14 of FIG. 13 showing that the thread type treated work-piece portions extend through the work-piece and are configured within the interior volume of the work-piece 80. FIG. 15 shows a cross-sectional view along line 15-15 of FIG. 13 showing that the thread type treated work-piece portions 132 extend through the work-piece from surface 110 to surface 110'. A thread type treated work-piece portion is elongated having a length 134 that is more than about 10 times a maximum cross-length dimension 135, as shown in FIG. 15. It is to be noted that the diameter or cross-section of a thread type treated work-piece portion may change over the length, wherein in a first location along the length the cross-dimension of the treated portion is greater than in a second location along the length.

FIG. 16 shows a perspective view of an exemplary neutron beam diffraction material treatment system 100 comprising a first neutron beam source 20 and a second neutron beam source 20' that are producing neutron beams 22, 22' respectively. The neutron beams are intersecting at intersection point 112 on a work-piece 80. Neutron beam source 20 and 20' are configured to rotate about two axes as indicated by the bold arrow around the axes lines. These two degrees of freedom enables the intersection point 112 to be moved from one location to another location. An intersecting point may be dynamically moved from a first position to a second position, wherein the work-piece is treated in between the first and second locations.

FIG. 17 shows a perspective view of a first neutron beam 26 and a second neutron beam 27 intersecting on a work-piece 80 to create neutron diffraction 122 and having an offset angle 120. The second neutron beam is offset from the first neutron beam by offset angle 120 which may be any suitable offset angle including more than about 5 degrees to 180 degrees. The X, Y, and Z axes are shown and it is to be understood that the neutron beam may be directed in any orientation along or between these axes.

FIG. 18 shows a perspective view of a neutron beam 26 and a second neutron beam 27 intersecting on a work-piece 80 to create neutron diffraction 122 and having an offset angle 120. In this embodiment, the second neutron beam is at a much lower offset angle than the embodiment shown in FIG. 17.

As shown in FIG. 19, an exemplary neutron beam regulator system 12 comprises a power control system 13 and a plurality of discrete magnetic coils 16-16" configured around a neutron beam 22 and extending substantially from the neutron beam source 20 to the target 19, or the neutron beam length 60. Each of the discrete magnetic coils has an individual power supply 35 and individual or discrete magnetic coil plugs 39. This magnetic coil configuration may be configured to both contain the neutron beam and also to modulate the neutron beam through changes in the magnetic field strength or direction. One or more of the discrete magnetic coils may be a modulating magnetic coil 17 and be coupled with a modulating coil output 37. A modulating magnetic coil controller 48 may be configured to enable a user to modulate the level and/or direction of the magnetic field 11 produced by one or more modulating magnetic coils 17. The electrical current running through the coils will produce a magnetic field as indicated by the spiral having an arrow around the coil 11' and will follow the principle of the "right hand rule". The modulating magnetic coil controller 48 is depicted as a dial but may be any suitable user input device including, but not limited to, a button, knob, computer input screen or field and the like. The power control system 13 is configured in a single power control housing 40 having a single plug for coupling with a power source 30, a neutron beam source power supply output 34 and one or more magnetic coil power supply outputs 35. The containment magnetic coils 15 may produce a magnetic field that that excludes neutrons from outside of the coils from entering and may steer or direct the outside neutrons away from the neutron beam regulator system 12

As shown in FIG. 20, an exemplary neutron beam regulator system 12 comprises a continuous magnetic coil 52 configured around a neutron beam and extending substantially the entire neutron beam length 60. The continuous magnetic coil is a spiraled coil 54 having a continuous length from a first end to a second end, or extending spiraling substantially the entire length of the neutron beam length 60. The continuous magnetic coil may be a containment magnetic coil 15 and may also be configured as a modulating magnetic coil 17. A user may run the neutron beam regulator system with a constant magnetic field intensity whereby the magnetic coil acts simply as a containment magnetic coil. In another embodiment, a user may vary the magnetic field intensity, thereby causing the magnetic coil to be a modulating magnetic coil 17. A neutron beam 22 exits the neutron source 20 at the neutron beam output 24 and extends to a target 19. The target is configured on a work-station 81 having an actuator 88 to move the target up into the magnetic field generated by the magnetic coil 15. The actuator may enable a user to load a work-station with a work-piece for processing and then actuate the part up into the magnetic coil. After the work-piece has been processed, the actuator may move the work-station down and from the magnetic coil to allow a user to remove the work-piece or target. This actuating work-station further reduces neutron radiation exposure by placing the work-piece within the magnetic field. The direction of the electrical current around the coils, as indicated by the arrows tangent with the magnetic coils, produces a magnetic field 11 that contains the neutron beam 22 and also directs it from the beam outlet 24 to the target 19.

As shown in FIG. 21, an exemplary neutron beam regulator system 12 comprises a continuous magnetic coil 52 configured partially around the neutron beam source 20 or generator. The magnetic coil 15 extends upstream of the neutron beam output, or the location where the beam exits the neutron beam generator. Again, this configuration reduces neutron radiation exposure by placing the neutron beam output 24 within the magnetic field.

As shown in FIG. 22, an exemplary neutron beam regulator system 12 comprises a continuous magnetic coil 52 configured partially around the neutron beam source 20 and partially around a work-piece station 81. The magnetic coil extends downstream of where the neutron beam hits the target or work-piece station. This configuration reduces neutron radiation exposure by placing both the neutron beam output 24 and the target within the magnetic field. It is to be understood that additional neutron absorbing material may be configured around the neutron source, the target or work-station, or along the neutron beam length. A magnetic coil may be configured in a housing that comprises neutron absorbing materials such as boron, for example.

As shown in FIG. 23, an exemplary power control system 13 comprises a power safety feature 43 comprising a magnetic coil power sensor 42 and a switch 44 that are configured to terminate power to a neutron beam source 20 in the event that no power, or a power level below some threshold power level, is being drawn by a containment magnetic coil 15. The switch 44 is in an open position and the neutron beam source is deactivated. As shown, the magnetic coil plug 38 is not plugged into the magnetic coil power supply output 35, and therefore no power is being drawn by the magnetic coil 15. A power safety feature may be configured with a magnetic coil power sensor that is coupled with one or more magnetic coil power supply outputs and specifically magnetic coils configured as containment magnetic coils. The neutron beam plug 39 is plugged into the neutron beam power supply output 34 but no power is provided. This safety feature ensures that the neutron beam will not be activated unless a containment magnetic coil is drawing power. A controller 46, such as a microprocessor may be configured to control the functions of the power control system.

As shown in FIG. 24, an exemplary power control system 13 comprises a power safety feature 43 that has enabled power supply to the neutron beam power supply output 34. The switch 44 is in a closed position and the neutron beam source 20 is activated, as the magnetic coil 15 is drawing power to contain the neutron beam 22.

As shown in FIG. 25, an exemplary neutron beam regulator system 12 comprises a containment magnetic coil 15 configured around a modulating magnetic coil 17. The containment magnetic coil is configured to reduce neutron radiation leakage from the system and the modulating magnetic coil is configured to change one or more properties of the neutron beam including, but not limited to, shape, intensity, velocity, direction and polarization. The modulating magnetic coil is inside of the containment magnetic coil in this embodiment. Any suitable combination of containment and modulating magnetic coils may be configured with a neutron beam regulator, as described herein. A containment magnetic coil may be a spiral coil that extends substantially the entire length of the neutron beam, and a modulating magnetic coil may be a discrete coil that is configured more proximal to the target. In another embodiment a modulating coil is a spiral coil that is configured proximal to the target but does not extend to the neutron beam generator. The neutron beam 22 is incident on a work-piece 80 that is configured on a work-piece station 81. A work-piece actuator 87 is configured to move the work-piece in one or more directions to change where the neutron beam hits the work-piece. As shown in FIG. 25, the work-piece actuator is configured to move the work-piece both back and forth, as indicated by the double-ended arrow, and also rotate the work-piece. These two actuation controls will enable the entire work-piece to be treated with the neutron beam. The incident location 89 of the neutron beam on the work-piece may be changed by actuation of the work-piece actuator to allow partial or complete surface treatment of the work-piece. A beam location program 98 is configured with the neutron beam regulator system 12 and enables positive tracking of a neutron beam on a work-piece as the work-piece is moved. A treatment program 99 is configured with the neutron beam regulator system 12 and enables modulation of the neutron beam as a function of position on the work-piece. A treatment program enables a work-piece to be treated with different levels of the neutron beam depending on the position on the work-piece.

As shown in FIG. 26, an exemplary work-piece 80 has areas treated with different levels of neutron bombardment through magnetic coil modulation as indicated by the different shaded areas of the work-piece. This work-piece has two apertures 86, 86', or bolt holes. This particular workpiece needs to be stiff in the areas 82, 84, around these fastening locations as indicated by the dark shaded areas. The work-piece however needs to be more supple, or less stiff, in the portion between the two apertures 83, as indicated by the lighter shading. The neutron beam regulator system, as described herein, enables this precise and controlled stiffening of a work-piece through modulated neutron bombardment. The neutron beam shape, intensity, velocity, direction and polarization may be modulated by a modulated magnetic coil as incident neutron beam location is changes over the work-piece.

As shown in FIG. 27, an exemplary neutron beam system 28 comprises an excluding magnetic coil 18 that is a continuous magnetic coil 52 configured around the neutron beam and extending substantially the entire neutron beam length 60. The continuous magnetic coil is a spiraled coil 54 having a continuous length from a first end to a second end, or extending spiraling substantially the entire length of the neutron beam length 60. The continuous magnetic coil is an excluding magnetic coil 18 and produces an excluding magnetic field 66 as indicated by the bold arrows. The excluding magnetic field substantially prevents outside neutrons 64 from entering into the coil area, interfering with the neutron beam or impacting the target 19. An excluding magnetic coil may be used in situations where the target is sensitive to neutron and any exposure to stray neutrons may interfere with the target or reflection/diffraction measured from said target. It is to be understood that an excluding magnetic coil may be added to any of the neutron beam regulator systems as defined herein. It is also to be understood that an excluding magnetic coil may be configured as a continuous or discrete coil and may extend at least partially around the target or neutron source output.

As shown in FIG. 28, a first beam 230 and second beam 240 have coherence 250 at a treatment location 201. A first beam generator 220 and second beam generator are offset from each other by an offset distance 235. Note that the first beam has a much lower frequency than the second beam. The first beam and second beam are coherent at the treatment location, the first and or second beam may be changed in frequency or amplitude to adjust a position of coherence and to treat a desired treatment location. In addition, the first and/or second beam generator may be adjusted in position, displaced in one more directions, to change the location of coherence.

As shown in FIG. 29, a first beam 230 has a first frequency and a second beam 240 has a second frequency that is higher than the first beam frequency. The first and second beams are coherent at a plurality of coherent locations 250, 250. The frequency of the second beam is substantially different from the frequency of the first beam, wherein the second beam has a frequency that is at least 20% greater the first beam.

As shown in FIG. 30, a first beam 230 has a first frequency and second amplitude and a second beam 240 has a second frequency and second amplitude that is higher that the first beam amplitude. The first and second beams are coherent at a plurality of coherent locations 250, 250. The first beam has an amplitude that is substantially less than the second beam, wherein the second beam has an amplitude that is at least 20% more that the first amplitude.

As shown in FIG. 31, a first beam 230 and second beam 240 have a coherence 250 over a number of periods.

As shown in FIG. 32, a first complex beam 231 has a frequency that changes as a function of time. The first beam also has a change in amplitude as a function of time. The first beam is defined by a complex wave equation, such as by Fourier Transform. As described herein, a control system may regulate a first and/or second beam to be defined by a complex wave equation. The complex beams or waves are defined by a complex wave equation, as defined herein and described in detail in the reference incorporated by reference herein. The beam 231 has a first time domain, or period of time, having a much higher frequency and amplitude that a second time domain, or second period of time. The beam may oscillate between these two domains as a function of time in predictable or controlled manner, as defined by a complex wave equation. A control system may utilize a computer program to modulate or change a wave frequency and/or amplitude or change a domain.

As shown in FIG. 33, an exemplary coherent beam treatment system 200 incorporates a control system 210 that has a first beam generator 220 and second beam generator 220 that produce a first beam 230 and second beam 240, respectively. A beam regulator 260 regulates the first beam 230 to be coherent 250 at a treatment location 201. It is to be understood that the first and second beam generators may be enclosed in a single housing or enclosure 207. One or more microprocessors 270 may incorporate at control program that provides instructions to the beam regulator(s). The control program may generate a beam defined by a complex wave, or a beam that changes frequency and/or amplitude as a function of time. A complex wave equation may utilize Fourier Transform.

As shown in FIG. 34, an exemplary coherent beam treatment system 200 incorporates a control system 210 that has a first beam generator 220 and second beam generator 220' that are offset by an offset distance 235c from each other and produce beams that intersect at a treatment location 201. The microprocessor 270 provides instructions to the beam regulators 260 to have the beams be coherent beams 250 at the treatment location 201.

As shown in FIG. 35, an exemplary coherent beam treatment system 200 incorporates a control system 210 comprising a microprocessor 270 that interfaces with the beam regulator to create beam coherence 250 at a treatment location 201. The microprocessor may utilize a computer program that establishes a complex wave equation, such as a Fourier transform equation and the like to produce a high energy beam that is a complex wave. The computer program may also provide equations for simple waves, having constant amplitude and frequency for one or more of the beams. As describe herein, the beams may have different amplitude and/or frequency however, or one may move with respect to the other or the treatment location. In this exemplary embodiment, a beam generator 260 produces an input beam 237 that is incident on a beam splitter 280, such as a prism 281. The beam splitter splits the input beam into a first split beam 231 and a second split beam 241. The second split beam 241 is incident on a mirror 290 that reflects and directs the second split beam to the treatment location. The first split beam and second split beam intersect with and are coherent with each other at the treatment location 201. The mirror may be moved by the control system to direct the second split beam. A user interface 214 is shown that may be used to provide inputs to the control system. A material input factor may be input into the system and this input may be used to control the first and or second beams, or split beams for transmission through the material 209.

As shown in FIG. 36, an exemplary coherent beam treatment system 200 incorporates a control system 210, a beam splitter 280 and a mirror 290. The second split beam is reflected by the mirror and then is received by a beam regulator. The second split beam may be regulated to produce coherence with the first split beam 231 at the treatment location 201. It is to be understood that the second split beam 241 may be received by a beam regulator before being incident on a mirror 290.

As shown in FIG. 37, a proton beam has a periodic high depth of penetration 295. A control system may regulate a proton beam such that the high depth of penetration is coherent with another beam at a treatment location.

As shown in FIG. 38, an exemplary spacecraft 326 is moving through outer space 320 and is propelled by an exemplary neutron propulsion device 300 comprising a neutron beam generator 220 and neutron beam source 20 as well as a magnetic coil 15 configured around the emitted neutron beam 22. The neutron beam is emitted from the spacecraft to produce thrust 350 and propel the spacecraft in a propulsion direction 355, as indicated by the bold arrows. The magnetic coils in this embodiment are self-contained magnets 51 requiring no supply of power to produce the magnetic field. As described herein a self-contained magnet may be natural magnets or neobdium magnets. The neutron beam shown in this embodiment is powered by a neutron beam power source 30. The magnetic coils may extend around the emitted neutron beam 22 from the beam outlet 24 from the generator to where the beam exits the spacecraft, or substantially along the length of the emitted beam within the spacecraft such as at least 80% of the length from the beam outlet 24 to exiting the spacecraft or at least 90% of the length.

As shown in FIG. 39, an exemplary self-contained spacecraft 321 is moving through space 320 and is propelled by an exemplary self-contained neutron propulsion device 301 comprising a neutron beam generator 220 and natural or self-contained neutron beam source 21 as well as a self-contained magnets 51 configured as magnetic coils 15 around the emitted neutron beam 22. The neutron beam is emitted from the spacecraft to produce thrust 350 and propel the spacecraft in a propulsion direction 355, as indicated by the bold arrows. The magnetic coils in this embodiment are self-contained magnets requiring no supply of power to produce the magnetic field. As described herein, a self-contained magnet may be natural magnets or neobdium magnets. The neutron beam shown in this embodiment is self-contained neutron beam source such as a radioactive material, Californium-252. Cesium-137 and polonium-beryllium (Po—Be).

As shown in FIGS. 40 and 41, an exemplary spacecraft 326 has a pair of neutron beam propulsion devices 300, 300' configured to propel and steer the spacecraft. The neutron propulsion devices comprise a direction device 390, configured to change the direction of the emitted neutron beam 22, and thereby steer the spacecraft. The neutron beam propulsion devices may be self-contained neutron beam propulsion devices as described herein.

As shown in FIG. 42, an exemplary spacecraft 326 has an exemplary neutron beam propulsion device 300. This spacecraft may orbit a planet, such as Earth and be a satellite 324, or may be propelled to travel through interspace or be an interplanetary spacecraft 328, such as a data gathering spacecraft for taking images and collecting data related to outer space and planets. The neutron beam propulsion device has a plurality of magnetic coils 15, configured around the neutron emitted neutron beam 22. The neutron beam source may be a self-contained neutron beam source 21 and the magnets may be self-contained magnets, as described herein, thereby producing a self-contained propulsion spacecraft 321.

Definition

The term space as used herein to describe the location of travel of a spacecraft is outside of the Earth's atmosphere, or outer space.

The term, coordinated actuation, as used herein, means that a first and second neutron beam are moved to create an intersecting point that moves along or within a work-piece.

A target is any object that a neutron may be incident on for treatment, analysis or conditioning, including neutron bombardment to stiffen or harden a material or work-piece. A target may be a person's tissue and particularly a tumor. A target may be a physical work-piece that is being analyzed or conditioned through neutron bombardment and may be a metal, plastic, ceramic, composite and the like.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

Fourier transform mathematical expressions, equations, and applications, including forms of differential equations and the use of Fourier transforms to create coherence are described in the following references, all of which are incorporated by reference herein:

Lectures Notes For, EE261: The Fourier Transform and its Application, Prof. Brad Osgood, Electrical Engineering Department, Stanford University (This document is provided with the filing of this application);

The Fourier Transform and its Application, Third Edition, Ronald N Bracewell ISBN-13: 978-0073039381. McGraw-Hill Science/Engineering/Math; Jun. 8, 1999;

Fourier Transforms; Ian N. Sneddon, ISBN-13: 080-0759685226, Dover Publications, Sep. 28, 2010;

Fourier transform representation of an ideal lens in coherent optical systems, (NASA technical report, NASA TR R-319), B0006CN02W, National Aeronautics and Space Administration; for sale by the Clearinghouse for Federal Scientific and Technical Information, Springfield, Va. (1970); sds Fourier Transforms and Imaging with Coherent Optical Systems, Okan K. Ersoy, John Wiley & Sons, Inc, 2007; and Linear Systems, Fourier Transforms, and Optics, Jack D. Gaskill, ISBN-13: 978-0471292883, Wiley-Interscience; 1 edition (June 1978).

What is claimed is:

1. A spacecraft comprising:
   a propulsion device comprising:
      neutron beam regulator system comprising:
         a magnetic coil configured around a neutron beam that is produced by a neutron beam source and emitted by a neutron beam generator;
         wherein the neutron beam is emitted from the spacecraft to propel the spacecraft in space.

2. The spacecraft of claim 1, wherein the neutron beam source is a generated neutron beam source and wherein the propulsion device comprises a power control system comprising:
   a neutron beam source power supply output.

3. The spacecraft of claim 1, wherein the magnetic coil is a power generated magnetic coil that produces a magnetic field through a supply of electrical power to the magnetic coils.

4. The spacecraft of claim 3, wherein the neutron beam regulator system comprises:
   a magnetic coil power supply output;
   a neutron beam source power supply output;
   magnetic coil power sensor;
   a power safety feature configured to prevent power supply to said neutron beam source power supply output when said magnetic coil power supply sensor detects that a power level below a threshold power level is being drawn from the magnetic coil power supply output;
   whereby the neutron beam generator will not receive power from the power control system unless the magnetic coil is drawing said threshold power level and producing a confining magnetic field.

5. The spacecraft of claim 1, wherein the neutron beam source is a self-contained neutron beam source.

6. The spacecraft of claim 5, wherein the magnetic coil is a power generated magnetic coil that produces a magnetic field through a supply of electrical power to the magnetic coils.

7. The spacecraft of claim 6, wherein the neutron beam regulator system comprises:
   a magnetic coil power supply output;
   magnetic coil power sensor;
   a power safety feature configured to prevent generation of the neutron beam from the neutron beam source when said magnetic coil power supply sensor detects that a power level below a threshold power level is being drawn from the magnetic coil power supply output;
   whereby the neutron beam generator will generate the neutron beam unless the magnetic coil is drawing said threshold power level and producing a confining magnetic field.

8. The spacecraft of claim 1, wherein the neutron beam source is a self-contained neutron beam source.

9. The spacecraft of claim 8, wherein the self-contained neutron beam source comprises Californium 252.

10. The spacecraft of claim 8, wherein the self-contained neutron beam source comprises Cesium-137.

11. The spacecraft of claim 8, wherein the self-contained neutron beam source comprises both Beryllium and Polonium.

12. The spacecraft of claim 8, wherein the magnetic coil is a self-contained magnetic coil that produces a magnetic field without a supply of electrical power to the magnetic coils.

13. The spacecraft of claim 9, wherein the self-contained magnetic coil comprises neobdium.

14. The spacecraft of claim 9, wherein the spacecraft is propelled without utilizing any electrical power.

15. The spacecraft of claim 9, wherein the spacecraft is self-contained propelled spacecraft that is propelled by the propulsion device without utilizing any electrical power.

16. The spacecraft of claim 1, wherein the magnetic coil is a substantially continuous coil that extends a length of the neutron beam.

17. The spacecraft of claim 16, wherein the magnetic coil extends substantially the length of the neutron beam, at least 80% of the length from a beam outlet to where the neutron beam exits the spacecraft.

18. The spacecraft of claim 1, comprising a plurality of magnetic coils configured to extend around a neutron beam.

19. The spacecraft of claim 18, wherein the plurality of magnetic coils are discrete coils having discrete coil power inputs.

20. The spacecraft of claim 1, wherein the magnetic coil extends upstream of a neutron beam output.

* * * * *